US012150627B2

(12) United States Patent
Peliks et al.

(10) Patent No.: US 12,150,627 B2
(45) Date of Patent: Nov. 26, 2024

(54) BONE BIOPSY DEVICE AND RELATED METHODS

(71) Applicant: Merit Medical Systems, Inc., South Jordan, UT (US)

(72) Inventors: Robert Bilgor Peliks, San Francisco, CA (US); Jeremy Snow, South Jordan, UT (US); Jade Ollerenshaw, North Melbourne (AU)

(73) Assignee: Merit Medical Systems, Inc., South Jordan, UT (US)

( * ) Notice: Subject to any disclaimer, the term of this patent is extended or adjusted under 35 U.S.C. 154(b) by 976 days.

(21) Appl. No.: 17/116,294

(22) Filed: Dec. 9, 2020

(65) Prior Publication Data

US 2021/0177386 A1 Jun. 17, 2021

Related U.S. Application Data

(60) Provisional application No. 62/946,830, filed on Dec. 11, 2019.

(51) Int. Cl.
*A61B 5/00* (2006.01)
*A61B 10/02* (2006.01)
(Continued)

(52) U.S. Cl.
CPC ........ *A61B 10/025* (2013.01); *A61B 10/0275* (2013.01); *A61B 17/3403* (2013.01); *A61B 17/3421* (2013.01); *A61B 17/3472* (2013.01); *A61B 2010/0208* (2013.01); *A61B 2010/0258* (2013.01); *A61B 2017/00398* (2013.01);
(Continued)

(58) Field of Classification Search
CPC .............. A61B 10/025; A61B 10/0275; A61B 17/3403; A61B 17/3421; A61B 17/3472; A61B 2010/0208; A61B 2010/0258; A61B 2017/00398; A61B 2017/3409; A61B 2560/0214; A61B 17/32002; A61B 2017/00017
See application file for complete search history.

(56) References Cited

U.S. PATENT DOCUMENTS 737,293 A 8/1903 Summerfeldt
1,585,934 A 12/1923 Muir
(Continued)

FOREIGN PATENT DOCUMENTS

CA 2683108 A1 4/2010
CA 2589569 C 11/2016
(Continued)

OTHER PUBLICATIONS

International Search Report and Written Opinion dated Jul. 2, 2009 for PCT/KR2009/006741.
(Continued)

*Primary Examiner* — May A Abouelela
(74) *Attorney, Agent, or Firm* — Dorsey & Whitney LLP

(57) ABSTRACT

Devices and methods used to obtain a core tissue samples are disclosed. The devices may be configured to drill into cortical bone and saw a hole into a bone lesion and/or bone marrow while obtaining the core tissue sample. The devices can include a motor and a transmission configured to rotate a trocar having a tip configured for drilling and an outer coax cannula having a cutting tip configured for sawing.

20 Claims, 16 Drawing Sheets

(51) Int. Cl.
 *A61B 17/34* (2006.01)
 *A61B 17/00* (2006.01)
(52) U.S. Cl.
 CPC ............... *A61B 2017/3409* (2013.01); *A61B 2560/0214* (2013.01)

(56) References Cited

U.S. PATENT DOCUMENTS

| | | |
|---|---|---|
| 1,512,474 A | 10/1924 | Michael et al. |
| 1,663,761 A | 2/1927 | Johnson |
| D149,464 S | 5/1948 | Adler |
| 2,850,007 A | 9/1958 | Lingley |
| 2,953,934 A | 9/1960 | Sundt |
| 3,001,522 A | 9/1961 | Irving |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,628,524 A | 12/1971 | Jamshidi |
| 3,630,192 A | 12/1971 | Jamshidi |
| 3,727,602 A | 4/1973 | Hayden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |
| 3,929,123 A | 12/1975 | Jamshidi |
| 4,010,737 A | 3/1977 | Vilaghy |
| 4,256,119 A | 3/1981 | Gauthier |
| 4,258,722 A | 3/1981 | Sessions et al. |
| 4,266,555 A | 5/1981 | Jamshidi |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,366,822 A | 1/1983 | Altshuler |
| 4,378,810 A | 4/1983 | Ishizaki et al. |
| 4,445,509 A | 5/1984 | Auth |
| 4,469,109 A | 9/1984 | Mehl |
| 4,487,209 A | 12/1984 | Mehl |
| 4,490,137 A | 12/1984 | Moukheibir |
| 4,513,754 A | 4/1985 | Lee |
| 4,549,554 A | 10/1985 | Markham |
| 4,557,265 A | 12/1985 | Anderson |
| 4,577,629 A | 3/1986 | Martinez |
| 4,589,414 A | 5/1986 | Yoshida et al. |
| 4,598,710 A | 7/1986 | Kleinberg et al. |
| 4,603,694 A | 8/1986 | Wheeler |
| 4,605,011 A | 8/1986 | Naslund |
| 4,617,430 A | 10/1986 | Bryant |
| 4,620,539 A | 11/1986 | Andrews et al. |
| 4,640,296 A | 2/1987 | Schnepp-Pesch |
| 4,643,197 A | 2/1987 | Greene et al. |
| 4,645,153 A | 2/1987 | Granzow et al. |
| 4,655,226 A | 4/1987 | Lee |
| 4,662,869 A | 5/1987 | Wright |
| 4,678,459 A | 7/1987 | Onik et al. |
| 4,683,885 A | 8/1987 | Hutterer et al. |
| 4,696,298 A | 9/1987 | Higgins et al. |
| 4,702,260 A | 10/1987 | Wang |
| 4,708,147 A | 11/1987 | Haaga |
| 4,776,346 A | 10/1988 | Beraha et al. |
| 4,798,213 A | 1/1989 | Doppelt |
| 4,838,282 A | 6/1989 | Strasser et al. |
| 4,844,087 A | 7/1989 | Garg |
| 4,850,354 A | 7/1989 | McGurk-Burleson et al. |
| 4,893,635 A | 1/1990 | De Groot et al. |
| 4,907,598 A | 3/1990 | Bauer |
| 4,922,602 A | 5/1990 | Mehl |
| RE33,258 E | 7/1990 | Onik et al. |
| 4,940,061 A | 7/1990 | Terwilliger et al. |
| 4,944,308 A | 7/1990 | Aug |
| 4,952,817 A | 8/1990 | Bolan et al. |
| 4,958,625 A | 9/1990 | Bates et al. |
| 4,967,762 A | 11/1990 | Devries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,040,542 A | 8/1991 | Gray |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,197,482 A * | 3/1993 | Rank ............... A61B 90/39 606/116 |
| 5,203,866 A | 4/1993 | Islam |
| 5,225,763 A | 7/1993 | Krohn et al. |
| 5,226,910 A | 7/1993 | Kajiyama et al. |
| 5,234,000 A | 8/1993 | Hakky et al. |
| 5,234,426 A * | 8/1993 | Rank ............... A61B 90/39 606/1 |
| 5,236,334 A | 8/1993 | Bennett |
| 5,249,583 A | 10/1993 | Mallaby |
| 5,251,641 A | 10/1993 | Xavier |
| 5,257,632 A | 11/1993 | Turkel et al. |
| 5,269,791 A | 12/1993 | Mayzels et al. |
| 5,279,306 A | 1/1994 | Mehl |
| 5,282,476 A | 2/1994 | Terwilliger |
| 5,282,477 A | 2/1994 | Bauer |
| 5,284,472 A | 2/1994 | Sussman et al. |
| 5,292,327 A | 3/1994 | Dodd et al. |
| 5,324,306 A | 6/1994 | Makower et al. |
| 5,331,972 A | 7/1994 | Wadhwani et al. |
| 5,334,183 A | 8/1994 | Wuchinich |
| 5,336,229 A | 8/1994 | Noda |
| 5,357,974 A | 10/1994 | Baldridge |
| 5,368,029 A | 11/1994 | Holcombe et al. |
| 5,368,045 A | 11/1994 | Clement et al. |
| 5,395,313 A | 3/1995 | Naves et al. |
| 5,400,798 A | 3/1995 | Baran |
| 5,409,013 A | 4/1995 | Clement |
| 5,439,474 A | 8/1995 | Li |
| 5,441,510 A | 8/1995 | Simpson et al. |
| 5,456,267 A | 10/1995 | Stark |
| 5,458,112 A | 10/1995 | Weaver |
| 5,469,860 A | 11/1995 | De Santis |
| 5,479,486 A | 12/1995 | Saji |
| 5,485,917 A | 1/1996 | Early |
| 5,492,130 A | 2/1996 | Chiou |
| 5,505,210 A | 4/1996 | Clement |
| 5,511,556 A | 4/1996 | De Santis |
| 5,526,821 A | 6/1996 | Jamshidi |
| 5,526,822 A | 6/1996 | Burbank et al. |
| 5,527,322 A | 6/1996 | Clement |
| 5,535,755 A | 7/1996 | Heske |
| 5,538,009 A | 7/1996 | Byrne et al. |
| 5,546,957 A | 8/1996 | Heske |
| 5,554,151 A | 9/1996 | Hinchliffe |
| 5,560,373 A | 10/1996 | De Santis |
| 5,562,685 A | 10/1996 | Mollenauer et al. |
| 5,564,436 A | 10/1996 | Hakky et al. |
| 5,569,035 A | 10/1996 | Balfour et al. |
| 5,569,277 A | 10/1996 | Evans et al. |
| 5,569,284 A | 10/1996 | Young et al. |
| 5,575,293 A | 11/1996 | Miller et al. |
| 5,578,030 A | 11/1996 | Levin |
| 5,582,616 A | 12/1996 | Bolduc et al. |
| 5,591,170 A | 1/1997 | Speivack et al. |
| 5,601,585 A | 2/1997 | Banik et al. |
| 5,602,449 A | 2/1997 | Krause et al. |
| 5,617,874 A | 4/1997 | Baran |
| 5,643,304 A | 7/1997 | Schechter et al. |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey |
| 5,699,909 A | 12/1997 | Foster |
| 5,700,265 A | 12/1997 | Romano |

(56) References Cited

U.S. PATENT DOCUMENTS

| | | | |
|---|---|---|---|
| 5,709,697 | A | 1/1998 | Ratcliff et al. |
| 5,720,760 | A | 2/1998 | Becker et al. |
| 5,735,264 | A | 4/1998 | Siczek et al. |
| 5,752,923 | A | 5/1998 | Terwilliger |
| 5,755,714 | A | 5/1998 | Murphy-Chutorian |
| 5,758,655 | A | 6/1998 | Como Rodriguez et al. |
| 5,766,135 | A | 6/1998 | Terwilliger |
| 5,769,086 | A | 6/1998 | Ritchart et al. |
| 5,769,795 | A | 6/1998 | Terwilliger |
| 5,775,333 | A | 7/1998 | Burbank et al. |
| 5,788,651 | A | 8/1998 | Weilandt |
| 5,792,167 | A | 8/1998 | Kablik et al. |
| 5,807,275 | A | 9/1998 | Jamshidi |
| 5,807,282 | A | 9/1998 | Fowler |
| 5,810,826 | A | 9/1998 | Ang et al. |
| 5,817,033 | A | 10/1998 | De Santis et al. |
| 5,817,034 | A | 10/1998 | Milliman et al. |
| 5,823,970 | A | 10/1998 | Terwilliger |
| 5,827,305 | A | 10/1998 | Gordon |
| 5,830,219 | A | 11/1998 | Bird et al. |
| D403,405 | S | 12/1998 | Terwilliger |
| 5,843,001 | A | 12/1998 | Goldenberg |
| 5,857,982 | A | 1/1999 | Milliman et al. |
| 5,879,365 | A | 3/1999 | Whitfield et al. |
| 5,908,233 | A | 6/1999 | Jeskett et al. |
| 5,913,857 | A | 6/1999 | Ritchart et al. |
| 5,916,198 | A | 6/1999 | Dillow |
| 5,916,229 | A | 6/1999 | Evans |
| 5,928,164 | A | 7/1999 | Burbank et al. |
| 5,944,673 | A | 8/1999 | Gregoire et al. |
| 5,951,490 | A | 9/1999 | Fowler |
| 5,951,575 | A | 9/1999 | Bolduc et al. |
| 5,964,716 | A | 10/1999 | Gregoire et al. |
| 5,971,939 | A | 10/1999 | De Santis et al. |
| 5,976,164 | A | 11/1999 | Bencini et al. |
| 5,980,469 | A | 11/1999 | Burbank et al. |
| 5,980,545 | A * | 11/1999 | Pacala ............... A61B 18/1482 606/171 |
| 6,007,495 | A | 12/1999 | Matula |
| 6,007,497 | A | 12/1999 | Huitema |
| 6,007,556 | A | 12/1999 | Kablik et al. |
| 6,017,316 | A | 1/2000 | Ritchart et al. |
| 6,018,227 | A | 1/2000 | Kumar et al. |
| 6,019,733 | A | 2/2000 | Farascioni |
| 6,022,324 | A | 2/2000 | Skinner |
| 6,022,325 | A | 2/2000 | Siczek et al. |
| 6,027,458 | A | 2/2000 | Janssens |
| 6,036,657 | A | 3/2000 | Milliman et al. |
| 6,050,955 | A | 4/2000 | Bryan et al. |
| 6,071,284 | A * | 6/2000 | Fox ............... A61B 17/1635 606/80 |
| 6,077,230 | A | 6/2000 | Gregoire et al. |
| 6,083,176 | A | 7/2000 | Terwilliger |
| 6,083,237 | A | 7/2000 | Huitema et al. |
| 6,086,544 | A | 7/2000 | Hibner et al. |
| 6,106,484 | A | 8/2000 | Terwilliger |
| 6,110,128 | A | 8/2000 | Andelin |
| 6,110,129 | A | 8/2000 | Terwilliger |
| 6,120,462 | A | 9/2000 | Hibner et al. |
| 6,123,957 | A | 9/2000 | Jernberg |
| 6,126,617 | A | 10/2000 | Weilandt et al. |
| 6,142,955 | A | 11/2000 | Farascioni et al. |
| 6,152,918 | A | 11/2000 | Padilla et al. |
| 6,162,187 | A | 12/2000 | Buzzard et al. |
| 6,165,136 | A | 12/2000 | Nishtala |
| 6,193,673 | B1 | 2/2001 | Viola et al. |
| 6,196,978 | B1 | 3/2001 | Weilandt et al. |
| 6,213,957 | B1 | 4/2001 | Milliman et al. |
| 6,220,248 | B1 | 4/2001 | Voegele et al. |
| 6,221,029 | B1 * | 4/2001 | Mathis ............... A61B 10/0233 600/564 |
| 6,228,039 | B1 | 5/2001 | Binmoeller |
| 6,231,522 | B1 | 5/2001 | Voegele et al. |
| 6,241,687 | B1 | 6/2001 | Voegele et al. |
| 6,267,759 | B1 | 7/2001 | Quick |
| 6,273,861 | B1 | 8/2001 | Bates et al. |
| 6,273,862 | B1 | 8/2001 | Privitera et al. |
| 6,280,398 | B1 | 8/2001 | Ritchart et al. |
| 6,280,399 | B1 | 8/2001 | Rossin et al. |
| 6,283,925 | B1 | 9/2001 | Terwilliger |
| 6,302,852 | B1 | 10/2001 | Fleming, III et al. |
| 6,312,394 | B1 | 11/2001 | Fleming, III |
| 6,322,523 | B2 | 11/2001 | Weilandt et al. |
| 6,328,701 | B1 | 12/2001 | Terwilliger |
| 6,331,166 | B1 | 12/2001 | Burbank et al. |
| 6,340,351 | B1 | 1/2002 | Goldenberg |
| 6,358,217 | B1 | 3/2002 | Bourassa |
| 6,361,504 | B1 | 3/2002 | Shin |
| 6,402,701 | B1 | 6/2002 | Kaplan et al. |
| 6,419,641 | B1 | 7/2002 | Mark et al. |
| 6,428,486 | B2 | 8/2002 | Ritchart et al. |
| 6,428,487 | B1 | 8/2002 | Burdorff et al. |
| 6,432,064 | B1 | 8/2002 | Hibner et al. |
| 6,432,065 | B1 | 8/2002 | Burdorff et al. |
| 6,436,054 | B1 | 8/2002 | Viola et al. |
| 6,443,910 | B1 | 9/2002 | Krueger et al. |
| 6,471,700 | B1 | 10/2002 | Burbank et al. |
| 6,478,751 | B1 | 11/2002 | Krueger et al. |
| 6,482,158 | B2 | 11/2002 | Mault |
| 6,485,436 | B1 | 11/2002 | Truckai et al. |
| 6,488,636 | B2 | 12/2002 | Bryan et al. |
| 6,527,736 | B1 | 3/2003 | Attinger et al. |
| 6,540,694 | B1 | 4/2003 | Van Bladel et al. |
| 6,540,761 | B2 | 4/2003 | Houser |
| 6,551,255 | B2 | 4/2003 | Van Bladel et al. |
| 6,554,778 | B1 | 4/2003 | Fleming, III |
| 6,554,779 | B2 | 4/2003 | Viola et al. |
| 6,585,664 | B2 | 7/2003 | Burdoff et al. |
| 6,585,694 | B1 | 7/2003 | Smith et al. |
| 6,638,235 | B2 | 10/2003 | Miller et al. |
| 6,656,133 | B2 | 12/2003 | Voegele et al. |
| 6,659,105 | B2 | 12/2003 | Burbank et al. |
| 6,659,338 | B1 | 12/2003 | Dittmann et al. |
| 6,683,439 | B2 | 1/2004 | Takano et al. |
| 6,689,072 | B2 | 2/2004 | Kaplan et al. |
| 6,695,786 | B2 | 2/2004 | Wang et al. |
| 6,712,773 | B1 | 3/2004 | Viola |
| 6,712,774 | B2 | 3/2004 | Voegele et al. |
| 6,730,043 | B2 | 5/2004 | Krueger et al. |
| 6,752,768 | B2 | 6/2004 | Burdorff et al. |
| 6,753,671 | B1 | 6/2004 | Harvey |
| 6,758,824 | B1 | 7/2004 | Miller et al. |
| 6,764,495 | B2 | 7/2004 | Lee et al. |
| 6,832,990 | B2 | 12/2004 | Kortenbach et al. |
| 6,849,080 | B2 | 2/2005 | Lee et al. |
| 6,875,183 | B2 | 4/2005 | Cervi |
| 6,908,440 | B2 | 6/2005 | Fisher |
| D508,458 | S | 8/2005 | Solland et al. |
| 6,926,676 | B2 | 8/2005 | Turturro et al. |
| 6,984,213 | B2 | 1/2006 | Horner et al. |
| 7,001,342 | B2 | 2/2006 | Faciszewski |
| 7,025,732 | B2 | 4/2006 | Thompson et al. |
| 7,033,324 | B2 | 4/2006 | Giusti et al. |
| 7,048,694 | B2 | 5/2006 | Mark et al. |
| D525,583 | S | 7/2006 | Vu |
| 7,081,123 | B2 | 7/2006 | Merboth et al. |
| 7,153,274 | B2 | 12/2006 | Stephens et al. |
| 7,189,206 | B2 | 3/2007 | Quick et al. |
| 7,189,207 | B2 | 3/2007 | Viola |
| 7,201,722 | B2 | 4/2007 | Krueger |
| 7,219,867 | B2 | 5/2007 | Kalis et al. |
| 7,226,424 | B2 | 6/2007 | Ritchart et al. |
| 7,252,641 | B2 | 8/2007 | Thompson et al. |
| 7,276,032 | B2 | 10/2007 | Hibner et al. |
| 7,311,673 | B2 | 12/2007 | Mueller, Jr. et al. |
| 7,328,794 | B2 | 2/2008 | Lubs et al. |
| 7,331,930 | B2 | 2/2008 | Faciszewski |
| 7,347,829 | B2 | 3/2008 | Mark et al. |
| 7,374,544 | B2 | 5/2008 | Freeman et al. |
| 7,397,654 | B2 | 7/2008 | Mori |
| 7,402,140 | B2 | 7/2008 | Spero et al. |
| 7,405,536 | B2 | 7/2008 | Watts |
| 7,407,054 | B2 | 8/2008 | Seiler et al. |
| 7,432,813 | B2 | 10/2008 | Postma |

(56) References Cited

U.S. PATENT DOCUMENTS

| | | |
|---|---|---|
| 7,452,367 B2 | 11/2008 | Rassman et al. |
| 7,464,040 B2 | 12/2008 | Joao |
| 7,473,232 B2 | 1/2009 | Teague |
| 7,481,775 B2 | 1/2009 | Weikel, Jr. et al. |
| 7,490,048 B2 | 2/2009 | Joao |
| 7,513,877 B2 | 4/2009 | Viola |
| 7,517,321 B2 | 4/2009 | McCullough et al. |
| 7,517,322 B2 | 4/2009 | Weikel, Jr. et al. |
| 7,648,466 B2 | 1/2010 | Stephens et al. |
| 7,670,299 B2 | 3/2010 | Beckman et al. |
| 7,670,328 B2 | 3/2010 | Miller |
| 7,699,850 B2 | 4/2010 | Miller |
| 7,717,861 B2 | 5/2010 | Weikel et al. |
| 7,727,164 B2 | 6/2010 | Cicenas et al. |
| 7,740,594 B2 | 6/2010 | Hibner |
| 7,740,596 B2 | 6/2010 | Hibner |
| 7,740,597 B2 | 6/2010 | Cicenas et al. |
| 7,762,961 B2 | 7/2010 | Heske et al. |
| 7,811,260 B2 | 10/2010 | Miller et al. |
| 7,815,642 B2 | 10/2010 | Miller |
| 7,828,746 B2 | 11/2010 | Teague |
| 7,850,620 B2 | 12/2010 | Miller et al. |
| 7,854,706 B2 | 12/2010 | Hibner |
| 7,883,476 B2 | 2/2011 | Miller et al. |
| 7,899,528 B2 | 3/2011 | Miller |
| 7,951,089 B2 | 5/2011 | Miller |
| 7,988,643 B2 | 8/2011 | Hoffmann et al. |
| 8,002,733 B2 | 8/2011 | Kraft et al. |
| 8,038,664 B2 | 10/2011 | Miller |
| 8,070,689 B2 | 12/2011 | Masseglia et al. |
| 8,070,690 B2 | 12/2011 | Ikehara et al. |
| 8,142,365 B2 | 3/2012 | Miller |
| 8,187,203 B2 | 5/2012 | McClellan |
| 8,251,917 B2 | 8/2012 | Almazan |
| 8,308,693 B2 | 11/2012 | Miller et al. |
| 8,343,072 B2 | 1/2013 | Bacon et al. |
| 8,357,104 B2 | 1/2013 | Moos et al. |
| 8,419,683 B2 | 4/2013 | Miller et al. |
| 8,439,846 B2 | 5/2013 | Zambelli |
| 8,444,573 B2 | 5/2013 | Flatland |
| 8,465,491 B2 | 6/2013 | Yedicka et al. |
| 8,480,632 B2 | 7/2013 | Miller et al. |
| 8,506,568 B2 | 8/2013 | Miller |
| 8,617,085 B2 | 12/2013 | Moran, Jr. |
| 8,641,715 B2 | 2/2014 | Miller |
| 8,656,929 B2 | 2/2014 | Miller et al. |
| 8,668,698 B2 | 3/2014 | Miller et al. |
| 8,672,954 B2 | 3/2014 | Oren et al. |
| 8,684,978 B2 | 4/2014 | Miller et al. |
| 8,690,791 B2 | 4/2014 | Miller |
| 8,715,287 B2 | 5/2014 | Miller |
| 8,728,005 B2 | 5/2014 | McClellan |
| 8,728,006 B2 | 5/2014 | McClellan |
| 8,734,363 B2 | 5/2014 | Bacon |
| 8,812,101 B2 | 8/2014 | Miller et al. |
| 8,834,417 B2 | 9/2014 | Moos et al. |
| 8,845,621 B2 | 9/2014 | Fojtik |
| 8,870,872 B2 | 10/2014 | Miller |
| 8,876,826 B2 | 11/2014 | Miller |
| 8,944,069 B2 | 2/2015 | Miller et al. |
| 8,974,410 B2 | 3/2015 | Miller et al. |
| 8,992,535 B2 | 3/2015 | Miller |
| 8,998,848 B2 | 4/2015 | Miller et al. |
| 9,072,543 B2* | 7/2015 | Miller ............... A61B 17/3472 |
| 9,078,637 B2 | 7/2015 | Miller |
| 9,226,732 B2 | 1/2016 | Azimpoor et al. |
| 9,237,906 B2 | 1/2016 | Janssens |
| 9,295,487 B2 | 3/2016 | Miller et al. |
| 9,314,228 B2 | 4/2016 | Miller |
| 9,314,270 B2 | 4/2016 | Miller |
| 9,332,970 B2* | 5/2016 | Beck ................. A61B 17/3403 |
| 9,393,031 B2 | 7/2016 | Miller |
| 9,402,602 B2 | 8/2016 | Lee |
| 9,414,815 B2 | 8/2016 | Miller et al. |
| 9,433,400 B2 | 9/2016 | Miller |
| 9,439,667 B2 | 9/2016 | Miller |
| 9,451,968 B2 | 9/2016 | Miller et al. |
| 9,504,477 B2 | 11/2016 | Miller et al. |
| 9,510,910 B2 | 12/2016 | Miller et al. |
| 9,545,243 B2 | 1/2017 | Miller et al. |
| 9,572,551 B2 | 2/2017 | Fumex |
| 9,615,816 B2 | 4/2017 | Woodward |
| 9,717,564 B2 | 8/2017 | Miller et al. |
| 9,717,847 B2 | 8/2017 | Miller et al. |
| 9,730,729 B2 | 8/2017 | Kilcoin et al. |
| 9,839,740 B2 | 12/2017 | Beamer et al. |
| 9,872,703 B2 | 1/2018 | Miller et al. |
| 9,883,853 B2 | 2/2018 | Woodward et al. |
| 9,949,755 B2* | 4/2018 | Hanson ............. A61B 17/3476 |
| 10,016,216 B2 | 7/2018 | Sauter |
| 10,052,111 B2 | 8/2018 | Miller et al. |
| 10,064,630 B2 | 9/2018 | Forman et al. |
| 10,064,671 B2* | 9/2018 | Sharkey ............ A61B 17/8811 |
| 10,092,320 B2 | 10/2018 | Morgan et al. |
| 10,130,343 B2 | 11/2018 | Miller et al. |
| 10,166,337 B2 | 1/2019 | Martz |
| 10,245,010 B2 | 4/2019 | Miller et al. |
| 10,258,783 B2 | 4/2019 | Miller et al. |
| 10,335,126 B2 | 7/2019 | Harrison et al. |
| 10,359,139 B2 | 7/2019 | Duck et al. |
| 10,413,282 B2 | 9/2019 | Miller |
| 10,492,830 B2 | 12/2019 | Miller |
| 10,493,261 B2 | 12/2019 | Solomon et al. |
| D879,956 S | 3/2020 | Klenner et al. |
| D901,006 S | 11/2020 | Bergeson |
| D905,234 S | 12/2020 | Nock et al. |
| D906,487 S | 12/2020 | Greep et al. |
| D910,184 S | 2/2021 | Orome |
| D910,854 S | 2/2021 | Cise |
| D917,396 S | 4/2021 | Assmann |
| D917,693 S | 4/2021 | Lev et al. |
| 10,980,568 B1* | 4/2021 | Murphy ............ A61B 17/8819 |
| 10,993,707 B2* | 5/2021 | McGillicuddy ...... A61B 10/025 |
| D921,161 S | 6/2021 | Laible |
| D921,169 S | 6/2021 | Cheng |
| 2001/0005778 A1 | 6/2001 | Ouchi |
| 2001/0007925 A1 | 7/2001 | Ritchart et al. |
| 2001/0011156 A1 | 8/2001 | Viola et al. |
| 2001/0012919 A1 | 8/2001 | Terwilliger |
| 2001/0014779 A1 | 8/2001 | Burbank et al. |
| 2001/0034530 A1 | 10/2001 | Malackowski et al. |
| 2001/0044595 A1 | 11/2001 | Reydel et al. |
| 2001/0047183 A1 | 11/2001 | Privitera et al. |
| 2002/0019596 A1 | 2/2002 | Eggers et al. |
| 2002/0042581 A1 | 4/2002 | Cervi |
| 2002/0045840 A1 | 4/2002 | Voegele et al. |
| 2002/0065474 A1 | 5/2002 | Mola |
| 2002/0067151 A1 | 6/2002 | Tanishita |
| 2002/0068878 A1 | 6/2002 | Jasonni et al. |
| 2002/0077646 A1 | 6/2002 | Truwit et al. |
| 2002/0082518 A1 | 6/2002 | Weiss et al. |
| 2002/0107043 A1 | 8/2002 | Adamson et al. |
| 2002/0120212 A1 | 8/2002 | Ritchart et al. |
| 2002/0151822 A1 | 10/2002 | Brudorff et al. |
| 2002/0156395 A1 | 10/2002 | Stephens et al. |
| 2003/0078586 A1* | 4/2003 | Shapira ............ A61B 17/1635 |
| | | 606/180 |
| 2003/0114875 A1 | 6/2003 | Sjostrom |
| 2003/0130593 A1 | 7/2003 | Gonzalez |
| 2003/0130677 A1 | 7/2003 | Whitman et al. |
| 2003/0163142 A1 | 8/2003 | Paltieli et al. |
| 2003/0225344 A1 | 12/2003 | Miller |
| 2003/0229293 A1 | 12/2003 | Hibner et al. |
| 2003/0233101 A1 | 12/2003 | Lubock et al. |
| 2004/0015079 A1 | 1/2004 | Berger et al. |
| 2004/0019297 A1 | 1/2004 | Angel |
| 2004/0030367 A1 | 2/2004 | Yamaki et al. |
| 2004/0049128 A1 | 3/2004 | Miller et al. |
| 2004/0054299 A1 | 3/2004 | Burdorff et al. |
| 2004/0092992 A1 | 5/2004 | Adams et al. |
| 2004/0127814 A1 | 7/2004 | Negroni |
| 2004/0133124 A1* | 7/2004 | Bates ................. A61B 10/0275 |
| | | 600/564 |
| 2004/0167427 A1 | 8/2004 | Quick et al. |

(56) References Cited

U.S. PATENT DOCUMENTS

| | | |
|---|---|---|
| 2004/0186393 A1 | 9/2004 | Leigh et al. |
| 2004/0215102 A1 | 10/2004 | Ikehara et al. |
| 2004/0215103 A1 | 10/2004 | Mueller et al. |
| 2004/0220495 A1 | 11/2004 | Cahir et al. |
| 2004/0249278 A1 | 12/2004 | Krause |
| 2004/0267157 A1 | 12/2004 | Miller et al. |
| 2005/0004492 A1 | 1/2005 | Burbank et al. |
| 2005/0004559 A1 | 1/2005 | Quick et al. |
| 2005/0010131 A1 | 1/2005 | Burbank et al. |
| 2005/0020909 A1 | 1/2005 | Moctezuma De La Barrera et al. |
| 2005/0027210 A1 | 2/2005 | Miller |
| 2005/0049489 A1 | 3/2005 | Foerster et al. |
| 2005/0049521 A1 | 3/2005 | Miller et al. |
| 2005/0080355 A1 | 4/2005 | Mark |
| 2005/0085838 A1 | 4/2005 | Thompson et al. |
| 2005/0101879 A1 | 5/2005 | Shidham et al. |
| 2005/0113715 A1 | 5/2005 | Scwindt et al. |
| 2005/0113716 A1 | 5/2005 | Mueller, Jr. et al. |
| 2005/0124914 A1 | 6/2005 | Dicarlo et al. |
| 2005/0124915 A1 | 6/2005 | Eggers et al. |
| 2005/0165328 A1 | 7/2005 | Heske et al. |
| 2005/0165404 A1 | 7/2005 | Miller |
| 2005/0177117 A1 | 8/2005 | Crocker et al. |
| 2005/0193451 A1 | 9/2005 | Quistgaard et al. |
| 2005/0203439 A1 | 9/2005 | Heske et al. |
| 2005/0209530 A1 | 9/2005 | Pflueger |
| 2005/0267383 A1 | 12/2005 | Groenke et al. |
| 2005/0275378 A1 | 12/2005 | Canino et al. |
| 2005/0277829 A1 | 12/2005 | Tsonton et al. |
| 2005/0277871 A1 | 12/2005 | Selis |
| 2006/0030784 A1 | 2/2006 | Miller et al. |
| 2006/0074344 A1 | 4/2006 | Hibner |
| 2006/0074345 A1 | 4/2006 | Hibner |
| 2006/0074346 A1 | 4/2006 | Hibner |
| 2006/0113958 A1 | 6/2006 | Lobert et al. |
| 2006/0116603 A1 | 6/2006 | Shibazaki et al. |
| 2006/0129063 A1 | 6/2006 | Thompson et al. |
| 2006/0173377 A1 | 8/2006 | McCullough et al. |
| 2006/0178666 A1 | 8/2006 | Cosman et al. |
| 2006/0184063 A1 | 8/2006 | Miller |
| 2006/0184188 A1* | 8/2006 | Li .................. A61B 17/1642 606/180 |
| 2006/0241515 A1 | 10/2006 | Jones et al. |
| 2006/0258953 A1 | 11/2006 | Lee |
| 2006/0258956 A1 | 11/2006 | Haberstich et al. |
| 2006/0276747 A1 | 12/2006 | Moos et al. |
| 2007/0010843 A1* | 1/2007 | Green ............... A61B 17/3421 606/167 |
| 2007/0016101 A1 | 1/2007 | Feldman et al. |
| 2007/0027407 A1 | 2/2007 | Miller |
| 2007/0032741 A1 | 2/2007 | Hibner et al. |
| 2007/0066987 A1 | 3/2007 | Scanlan, Jr. |
| 2007/0073326 A1 | 3/2007 | Miller et al. |
| 2007/0090788 A1 | 4/2007 | Hansford et al. |
| 2007/0093841 A1 | 4/2007 | Hoogland |
| 2007/0106176 A1 | 5/2007 | Mark et al. |
| 2007/0118049 A1 | 5/2007 | Viola |
| 2007/0149894 A1 | 6/2007 | Heske et al. |
| 2007/0161925 A1 | 7/2007 | Quick et al. |
| 2007/0167782 A1 | 7/2007 | Callahan et al. |
| 2007/0179401 A1 | 8/2007 | Hibner |
| 2007/0213590 A1 | 9/2007 | Squicciarina |
| 2007/0213630 A1 | 9/2007 | Beckman et al. |
| 2007/0213632 A1 | 9/2007 | Okazaki et al. |
| 2007/0219572 A1 | 9/2007 | Deck et al. |
| 2007/0236180 A1 | 10/2007 | Rodgers |
| 2007/0239067 A1 | 10/2007 | Hibner et al. |
| 2007/0255173 A1 | 11/2007 | Hibner |
| 2007/0270710 A1 | 11/2007 | Frass et al. |
| 2007/0270712 A1 | 11/2007 | Wiksell et al. |
| 2007/0276288 A1 | 11/2007 | Khaw |
| 2007/0276352 A1 | 11/2007 | Crocker et al. |
| 2007/0287933 A1 | 12/2007 | Phan et al. |
| 2007/0293788 A1 | 12/2007 | Entrekin et al. |
| 2008/0004545 A1 | 1/2008 | Garrison |
| 2008/0007217 A1 | 1/2008 | Riley |
| 2008/0015429 A1 | 1/2008 | Tsonton et al. |
| 2008/0021487 A1 | 1/2008 | Heisler |
| 2008/0021488 A1 | 1/2008 | Berberich |
| 2008/0030170 A1 | 2/2008 | Dacquay et al. |
| 2008/0045857 A1* | 2/2008 | Miller .................. A61B 10/025 600/566 |
| 2008/0045861 A1* | 2/2008 | Miller .................... A61B 46/00 206/370 |
| 2008/0045965 A1* | 2/2008 | Miller .................. A61B 10/025 606/80 |
| 2008/0064925 A1 | 3/2008 | Gill et al. |
| 2008/0064984 A1 | 3/2008 | Pflueger |
| 2008/0071193 A1 | 3/2008 | Reuber et al. |
| 2008/0079391 A1 | 4/2008 | Schroeck et al. |
| 2008/0110261 A1 | 5/2008 | Randall et al. |
| 2008/0135443 A1 | 6/2008 | Frojd et al. |
| 2008/0139961 A1 | 6/2008 | Slama et al. |
| 2008/0146962 A1 | 6/2008 | Ritchie et al. |
| 2008/0146965 A1 | 6/2008 | Privitera et al. |
| 2008/0154151 A1 | 6/2008 | Ritchart et al. |
| 2008/0161682 A1 | 7/2008 | Kendrick et al. |
| 2008/0161718 A1 | 7/2008 | Schwindt |
| 2008/0161719 A1 | 7/2008 | Miller et al. |
| 2008/0161720 A1 | 7/2008 | Nicoson |
| 2008/0183099 A1 | 7/2008 | Jorgensen et al. |
| 2008/0195066 A1 | 8/2008 | Speeg et al. |
| 2008/0200833 A1 | 8/2008 | Hardin et al. |
| 2008/0200836 A1 | 8/2008 | Speeg et al. |
| 2008/0208194 A1 | 8/2008 | Bichenbach |
| 2008/0215056 A1* | 9/2008 | Miller .............. A61B 17/32002 606/80 |
| 2008/0221443 A1 | 9/2008 | Ritchie et al. |
| 2008/0221444 A1 | 9/2008 | Ritchie et al. |
| 2008/0221478 A1 | 9/2008 | Ritchie et al. |
| 2008/0221479 A1 | 9/2008 | Ritchie et al. |
| 2008/0221480 A1 | 9/2008 | Hibner et al. |
| 2008/0223904 A1 | 9/2008 | Marczyk |
| 2008/0228103 A1 | 9/2008 | Ritchie et al. |
| 2008/0228104 A1 | 9/2008 | Uber et al. |
| 2008/0232604 A1 | 9/2008 | Dufresne et al. |
| 2008/0234715 A1 | 9/2008 | Pescue et al. |
| 2008/0243163 A1 | 10/2008 | Masseglia |
| 2008/0262383 A1 | 10/2008 | Routhier et al. |
| 2008/0281225 A1 | 11/2008 | Spero et al. |
| 2008/0287826 A1 | 11/2008 | Videbaek et al. |
| 2008/0287859 A1 | 11/2008 | Miller et al. |
| 2008/0306404 A1 | 12/2008 | Ronald |
| 2008/0306405 A1 | 12/2008 | Masseglia et al. |
| 2008/0306406 A1 | 12/2008 | Thompson et al. |
| 2008/0308607 A1 | 12/2008 | Timm et al. |
| 2008/0312554 A1 | 12/2008 | Garrison |
| 2008/0319341 A1 | 12/2008 | Taylor et al. |
| 2009/0030405 A1 | 1/2009 | Quick et al. |
| 2009/0048533 A1 | 2/2009 | Miller |
| 2009/0062624 A1 | 3/2009 | Neville |
| 2009/0088666 A1 | 4/2009 | Miller et al. |
| 2009/0118641 A1 | 5/2009 | Van Dam et al. |
| 2009/0125062 A1 | 5/2009 | Arnin |
| 2009/0137927 A1 | 5/2009 | Miller |
| 2009/0171243 A1 | 7/2009 | Hibner et al. |
| 2009/0204021 A1 | 8/2009 | Shabaz et al. |
| 2009/0082695 A1 | 9/2009 | Whitehead |
| 2009/0227893 A1 | 9/2009 | Coonahan et al. |
| 2010/0030020 A1 | 2/2010 | Sanders et al. |
| 2010/0030105 A1 | 2/2010 | Noishiki et al. |
| 2010/0063416 A1 | 3/2010 | Cicenas et al. |
| 2010/0064393 A1 | 3/2010 | Berka et al. |
| 2010/0069790 A1 | 3/2010 | Green |
| 2010/0113972 A1 | 5/2010 | Alvarado |
| 2010/0152611 A1 | 6/2010 | Parihar et al. |
| 2010/0160820 A1 | 6/2010 | Weikel, Jr. et al. |
| 2010/0204649 A1 | 8/2010 | Miller et al. |
| 2010/0210966 A1 | 8/2010 | Videbaek |
| 2010/0234760 A1 | 9/2010 | Almazan |
| 2010/0292607 A1 | 11/2010 | Moore et al. |
| 2010/0312140 A1 | 12/2010 | Smith et al. |
| 2010/0317995 A1 | 12/2010 | Hibner et al. |
| 2010/0317997 A1 | 12/2010 | Hibner et al. |

(56) References Cited

U.S. PATENT DOCUMENTS

| | | |
|---|---|---|
| 2010/0317998 A1 | 12/2010 | Hibner et al. |
| 2011/0071391 A1 | 3/2011 | Speeg |
| 2011/0082387 A1 | 4/2011 | Miller et al. |
| 2011/0152715 A1 | 6/2011 | Delap et al. |
| 2011/0160611 A1 | 6/2011 | Ritchart et al. |
| 2011/0224577 A1 | 9/2011 | Park |
| 2011/0313316 A1 | 12/2011 | Ranpura et al. |
| 2012/0109061 A1 | 5/2012 | Miller et al. |
| 2012/0116248 A1 | 5/2012 | McWeeney et al. |
| 2012/0130274 A1 | 5/2012 | Persat |
| 2012/0197157 A1 | 8/2012 | Ryan et al. |
| 2012/0253228 A1 | 10/2012 | Schembre et al. |
| 2013/0041345 A1 | 2/2013 | Kilcoin et al. |
| 2013/0096508 A1 | 4/2013 | Beamer et al. |
| 2013/0096561 A1 | 4/2013 | Miller et al. |
| 2013/0204160 A1 | 8/2013 | McKenna et al. |
| 2014/0100448 A1 | 4/2014 | Neilan |
| 2014/0171826 A1* | 6/2014 | Lampropoulos ... A61B 10/0266 600/562 |
| 2014/0207021 A1 | 7/2014 | Snow |
| 2014/0221870 A1 | 8/2014 | McClellan |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward |
| 2014/0276839 A1 | 9/2014 | Forman et al. |
| 2014/0343454 A1 | 11/2014 | Miller et al. |
| 2015/0127006 A1 | 5/2015 | Miller |
| 2015/0129456 A1 | 5/2015 | Miller et al. |
| 2015/0223786 A1* | 8/2015 | Morgan ............... A61B 10/025 600/567 |
| 2015/0230823 A1* | 8/2015 | Morgan ............. A61B 17/3476 604/272 |
| 2015/0351797 A1 | 12/2015 | Miller et al. |
| 2016/0022282 A1* | 1/2016 | Miller ................ A61B 17/1615 606/80 |
| 2016/0030013 A1 | 2/2016 | Harrison, IV et al. |
| 2016/0030016 A1 | 2/2016 | McWeeney et al. |
| 2016/0058432 A1 | 3/2016 | Miller |
| 2016/0066954 A1 | 3/2016 | Miller et al. |
| 2016/0081678 A1 | 3/2016 | Kappel et al. |
| 2016/0174950 A1 | 6/2016 | Rusnak |
| 2016/0183974 A1 | 6/2016 | Miller |
| 2016/0184509 A1 | 6/2016 | Miller et al. |
| 2016/0206346 A1 | 7/2016 | Miller |
| 2016/0317133 A1 | 11/2016 | Orts et al. |
| 2016/0354067 A1 | 12/2016 | Rohl et al. |
| 2016/0367287 A1* | 12/2016 | Fumex ............... A61B 17/3476 |
| 2016/0367288 A1* | 12/2016 | Miller ................... A61B 17/34 |
| 2016/0374722 A1 | 12/2016 | Miller |
| 2017/0007271 A1 | 1/2017 | Miller et al. |
| 2017/0035397 A1 | 2/2017 | Miller et al. |
| 2017/0056029 A1 | 3/2017 | Wolters et al. |
| 2017/0333011 A1 | 11/2017 | Peliks |
| 2017/0340401 A1* | 11/2017 | Miller ................... A61B 50/30 |
| 2018/0085144 A1* | 3/2018 | McGillicuddy .... A61B 10/0266 |
| 2018/0092633 A1* | 4/2018 | Peliks ............. A61B 10/0266 |
| 2018/0125465 A1* | 5/2018 | Muse ................. A61B 10/025 |
| 2018/0256209 A1* | 9/2018 | Muse ................ A61B 17/3496 |
| 2018/0333145 A1 | 11/2018 | Snow |
| 2018/0333146 A1 | 11/2018 | Hallisey et al. |
| 2018/0333147 A1 | 11/2018 | Snow et al. |
| 2018/0344993 A1 | 12/2018 | Ganz et al. |
| 2019/0038345 A1* | 2/2019 | Pellegrino ............. A61B 18/18 |
| 2019/0090861 A1 | 3/2019 | Snow et al. |
| 2019/0117201 A1* | 4/2019 | Beck .................... A61B 10/025 |
| 2019/0142398 A1 | 5/2019 | Ranpura et al. |
| 2019/0328370 A1* | 10/2019 | Muse ................. A61B 10/0266 |
| 2019/0365360 A1* | 12/2019 | Vetter ................ A61B 10/0266 |
| 2020/0197044 A1* | 6/2020 | Fayne ................ A61B 17/3472 |
| 2020/0268362 A1* | 8/2020 | Van Liere .......... A61B 10/0266 |
| 2021/0093305 A1 | 4/2021 | Peliks et al. |
| 2021/0121201 A1* | 4/2021 | Tierney ............... A61B 10/0275 |
| 2021/0177386 A1 | 6/2021 | Peliks et al. |
| 2021/0275154 A1 | 9/2021 | Peliks et al. |

FOREIGN PATENT DOCUMENTS

| | | |
|---|---|---|
| CN | 107920808 A | 4/2018 |
| DE | 2848314 | 10/1979 |
| DE | 3924291 | 1/1991 |
| DE | 4120329 | 1/1992 |
| DE | 4041614 | 10/1992 |
| DE | 2453058 | 5/1996 |
| DE | 10034297 | 4/2001 |
| DE | 10026303 | 2/2002 |
| DE | 20209525 | 11/2002 |
| DE | 10235480 | 2/2004 |
| DE | 202009003224 U1 | 6/2009 |
| EP | 0433717 | 6/1991 |
| EP | 541377 | 5/1993 |
| EP | 0890339 | 1/1999 |
| EP | 0995400 | 4/2000 |
| EP | 1074271 | 2/2001 |
| EP | 1520518 | 4/2005 |
| EP | 1579809 | 9/2005 |
| EP | 1665958 | 6/2006 |
| EP | 2095772 | 2/2009 |
| EP | 2106750 | 10/2009 |
| FR | 1345429 | 12/1963 |
| FR | 2739293 | 4/1997 |
| GB | 2018601 | 10/1979 |
| GB | 2038640 | 12/1979 |
| GB | 21300890 | 6/1984 |
| JP | 09510630 | 10/1997 |
| JP | H10508504 | 8/1998 |
| JP | 2005530554 | 10/2005 |
| JP | 2006509545 | 3/2006 |
| JP | 2006528907 | 12/2006 |
| JP | 2007502159 | 2/2007 |
| RU | 2212848 | 11/2002 |
| SU | 1454457 | 1/1989 |
| WO | 199314700 | 8/1993 |
| WO | 199416181 | 7/1994 |
| WO | 199428801 | 12/1994 |
| WO | 199628097 | 9/1996 |
| WO | 199825522 | 6/1998 |
| WO | 199831285 | 7/1998 |
| WO | 199835615 | 8/1998 |
| WO | 199846290 | 10/1998 |
| WO | 199933501 | 7/1999 |
| WO | 200004832 | 2/2000 |
| WO | 200030546 | 6/2000 |
| WO | 200059378 | 10/2000 |
| WO | 200128439 | 4/2001 |
| WO | 200172230 | 10/2001 |
| WO | 2001078590 | 10/2001 |
| WO | 200222023 | 3/2002 |
| WO | 200232318 | 4/2002 |
| WO | 2002069808 | 9/2002 |
| WO | 2004075728 | 9/2004 |
| WO | 2004082489 | 9/2004 |
| WO | 20040757719 | 9/2004 |
| WO | 2005013830 | 2/2005 |
| WO | 2006015302 | 2/2006 |
| WO | 2006061514 | 6/2006 |
| WO | 2007047128 | 4/2007 |
| WO | 2007095330 | 8/2007 |
| WO | 2007112751 | 10/2007 |
| WO | 2008021687 | 2/2008 |
| WO | 2008024684 | 2/2008 |
| WO | 200804812 | 4/2008 |
| WO | 2008131362 | 10/2008 |
| WO | 2010107424 | 9/2010 |
| WO | 2010138944 A2 | 12/2010 |
| WO | 2012088167 A2 | 6/2012 |
| WO | 2014142948 | 9/2014 |
| WO | 2016196536 A1 | 12/2016 |
| WO | 2017046531 | 3/2017 |

(56) References Cited

FOREIGN PATENT DOCUMENTS

| WO | 2019049098 | 3/2019 |
|----|------------|--------|
| WO | 2010096139 | 8/2021 |

OTHER PUBLICATIONS

International Search Report and Written Opinion dated Sep. 4, 2018 for PCT/US2018/033188.
Office Action dated May 12, 2020 for U.S. Appl. No. 15/982,624.
Office Action dated May 12, 2020 for U.S. Appl. No. 15/982,777.
Office Action dated Jul. 1, 2020 for U.S. Appl. No. 15/980,116.
Office Action dated Nov. 17, 2020 for U.S. Appl. No. 15/982,624.
Office Action dated Nov. 27, 2020 for U.S. Appl. No. 15/982,777.
Office Action dated Oct. 20, 2023 for U.S. Appl. No. 17/032,869.
Notice of Allowance dated Jul. 9, 2021 for U.S. Appl. No. 15/982,624.
Notice of Allowance dated Aug. 25, 2021 for U.S. Appl. No. 15/965,109.
European Search Report dated Feb. 1, 2021 for EP18802126.5.
Notice of Allowance dated Jun. 16, 2021 for U.S. Appl. No. 29/722,920.
Office Action dated Jan. 12, 2023 for U.S. Appl. No. 17/032,869.
International Search Report and Written Opinion dated Jan. 8, 2021 for PCT/US2020/052779.
International Search Report and Written Opinion dated Apr. 7, 2021 for PCT/US2020/063934.
Office Action dated May 16, 2023 for U.S. Appl. No. 17/032,869.
International Search Report and Written Opinion fated Feb. 27, 2022 for PCT/US2022/072799.
International Search Report and Written Opinion dated Jun. 23, 2021 for PCT/US2021/020599.
Office Action dated Jul. 11, 2023 for U.S. Appl. No. 17/190,123.
Office Action dated Nov. 3, 2023 for U.S. Appl. No. 17/190,123.
Office Action dated Feb. 27, 2024 for U.S. Appl. No. 17/032,869.
Office Action dated Mar. 4, 2024 for U.S. Appl. No. 17/190,123.
Office Action dated Aug. 22, 2024 for U.S. Appl. No. 17/032,869.
Office Action dated Sep. 4, 2024 for U.S. Appl. No. 17/190,123.

\* cited by examiner

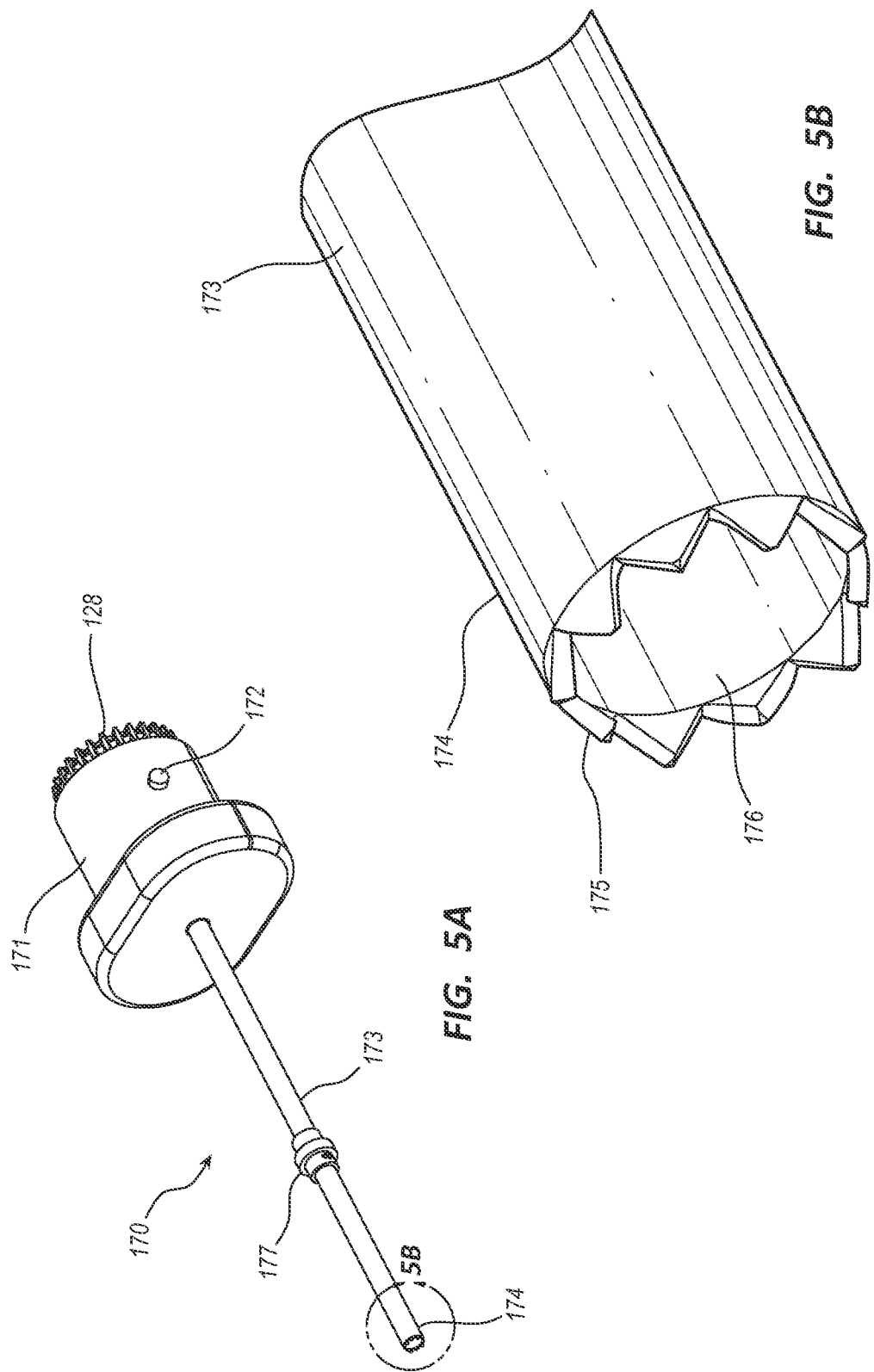

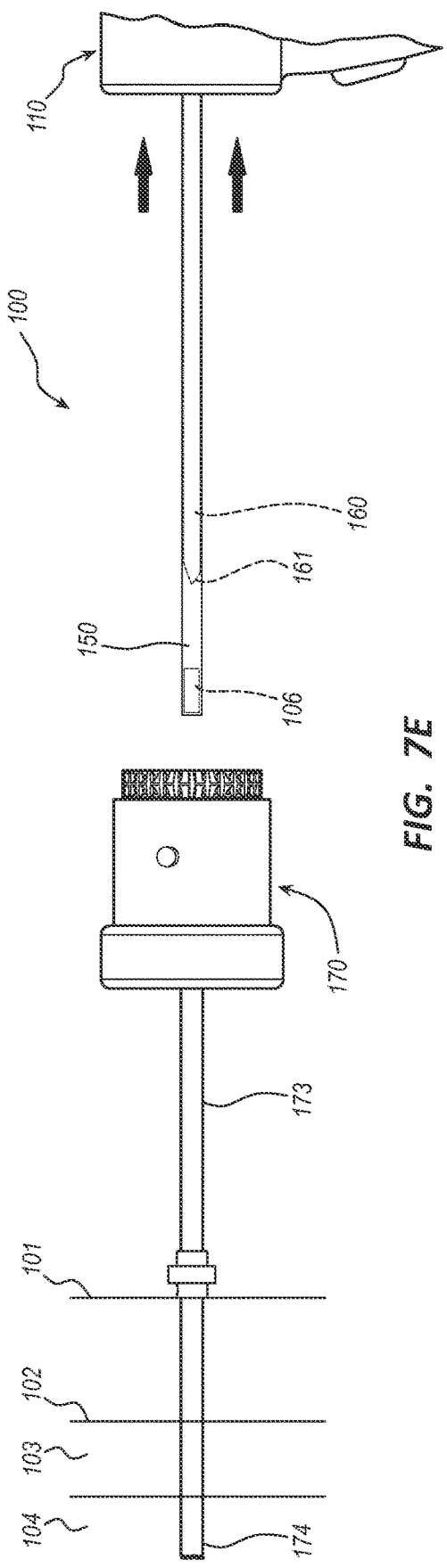
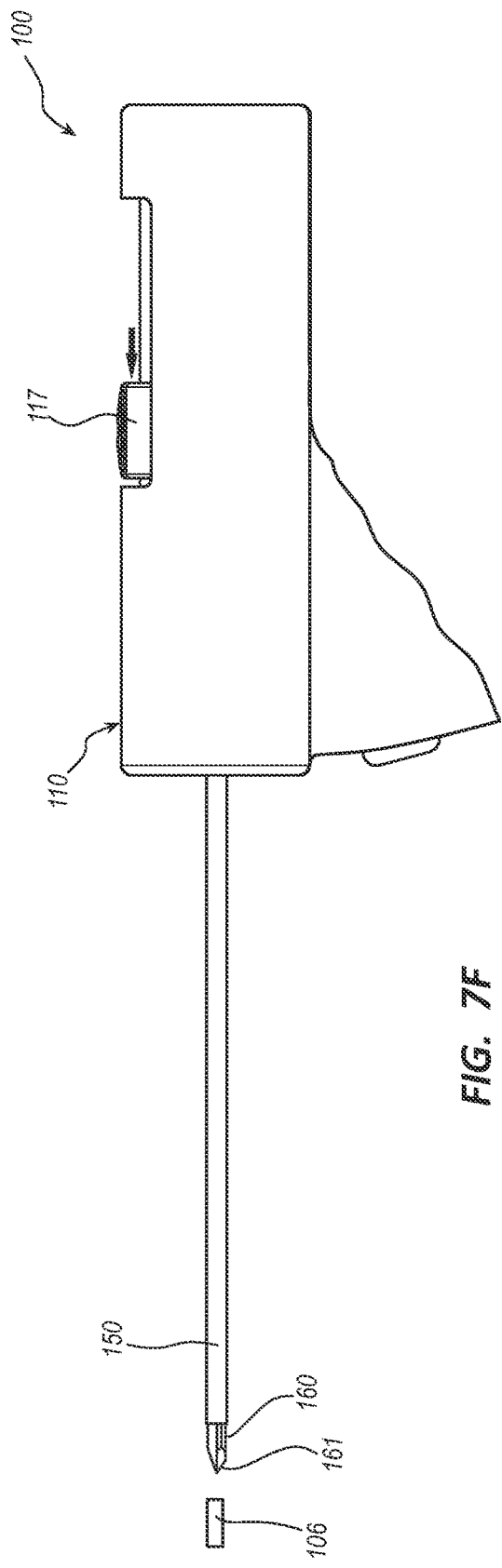
FIG. 7E
FIG. 7F

BONE BIOPSY DEVICE AND RELATED METHODS

RELATED APPLICATIONS

This application claims priority to U.S. Provisional Patent Application No. 62/946,830, filed Dec. 11, 2019, and titled BONE BIOPSY DEVICE AND RELATED METHODS, which is incorporated herein by reference in its entirety.

TECHNICAL FIELD

The present disclosure relates generally to devices used to perform a biopsy procedure, specifically a bone biopsy procedure. More specifically, the present disclosure relates to devices used to drill into a bone to obtain a core tissue sample of a bone lesion and/or bone marrow.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 5A is a perspective view of an outer coax cannula assembly of the bone biopsy device of FIG. 1.

FIG. 5B is a detailed view of a cutting tip of the outer coax cannula assembly of FIG. 5A.

FIG. 7E is a side view of the bone biopsy device of FIG. 1 with the inner cannula removed from an outer coax cannula.

FIG. 7F is a side view of the bone biopsy device of FIG. 1 with a tissue sample ejected from the inner cannula.

DETAILED DESCRIPTION

Figure 1:
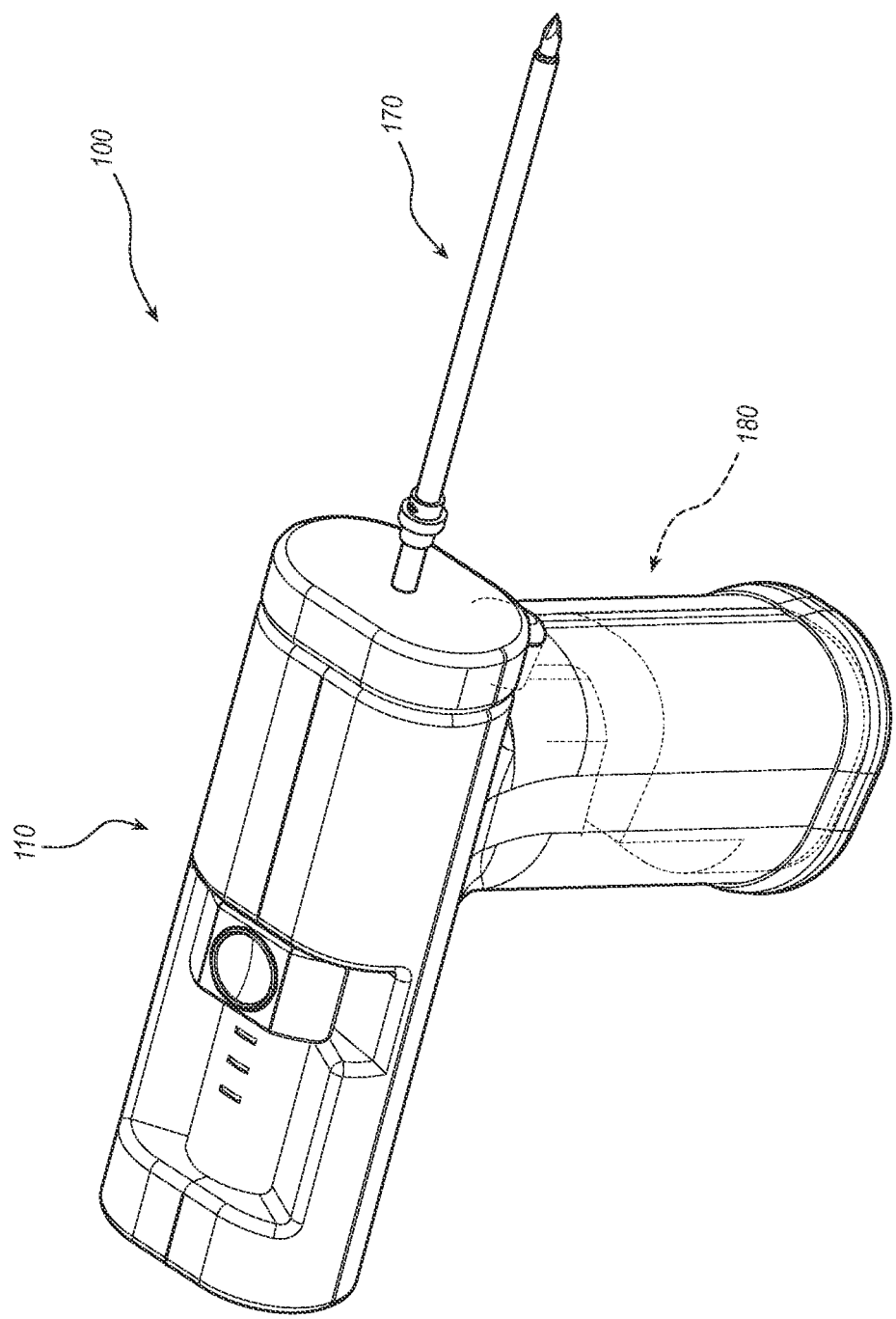
FIG. 1 is a perspective view of an embodiment of a bone biopsy device.

A bone biopsy device may include a handle assembly, a coax assembly, and a power pack. The handle assembly may include a housing configured to hold an inner cannula. The inner cannula may extend distally from the housing and may be configured to receive a core tissue sample. A trocar with a penetrating tip may be slidably disposed within a lumen of the inner cannula. The housing may include a slider member that is configured to displace the trocar relative to the inner cannula from a retracted configuration to an extended configuration where the trocar can drill into a bone. A motor and a transmission may rotate the inner cannula and the trocar. In certain instances, the transmission may include a worm drive. In other instances, the transmission may include a plurality of spur gears. The inner cannula and trocar may be configured to remain part of the handle assembly (e.g., coupled to the housing) before, during, and after a biopsy procedure. The coax assembly may be selectively detachable from the handle assembly. The coax assembly may include an outer coax cannula extending distally from a coax connector. The inner cannula may be partially disposed within a lumen of the outer coax cannula. The outer coax cannula can be rotated by the motor. A tip of the outer coax cannula may be a cutting tip (e.g., a trephine tip) and be configured to saw into a bone lesion and/or bone marrow. The power pack may be selectively removable from the handle assembly such that the power pack may be a reusable component. The power pack may comprise a power source, a controller, and a connector. The power pack and/or controller may also comprise a printed circuit board. In some instances, the motor may also be selectively removable from the handle assembly such that the motor may also be a reusable component (for instance, the motor may be selectively removable with the power pack).

The bone biopsy device may be used by a practitioner to obtain a core tissue sample of a bone lesion and/or bone marrow. In other instances, the bone biopsy device may be used to obtain a core tissue sample of other tissues within a patient, such as a soft tissue sample. In use, the trocar, outer coax cannula, and inner cannula may be rotated by the motor and drilled into the cortical bone layer adjacent to a lesion and/or bone marrow. The trocar may be retracted, and the inner cannula and the outer coax cannula rotated to saw a core tissue sample of the lesion and/or bone marrow that is collected in the inner cannula. The outer coax cannula may be removed from the inner cannula and the trocar advanced within the inner cannula to eject the core tissue sample. A needle or aspiration needle can also be inserted into the outer coax cannula to collect or aspirate bone marrow, blood, and/or tissue cells. A needle could also be inserted into the outer coax cannula to infuse or inject a substance (such as a medicament) into the patient.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to the bone biopsy device, the proximal end of the device refers to the end nearest the handle and the distal end refers to the opposite end, the end nearest the end of the outer coax cannula. Thus, if at one or more points in a procedure a physician changes the orientation of the device, as used herein, the term "proximal end" always refers to the handle end of the device (even if the distal end is temporarily closer to the physician).

FIGS. 1-10 illustrate different views of bone biopsy devices and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-7G depict one embodiment of a bone biopsy device 100. The bone biopsy device 100 includes three general groups of components; each group may have numerous subcomponents and parts. The three general component groups are: a handle assembly 110, a coax assembly 170, and a power pack 180 as illustrated in FIG. 1.

Figure 2:
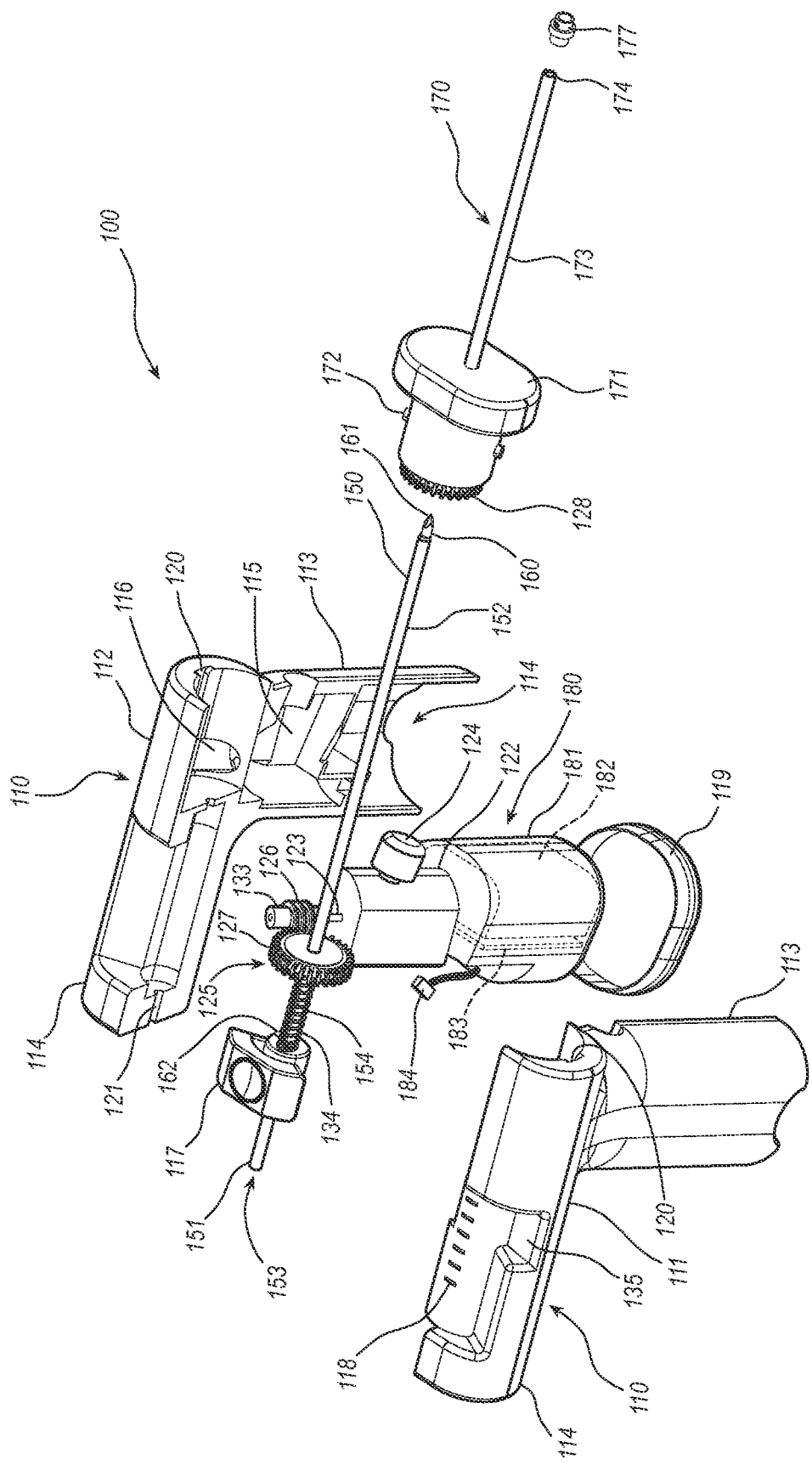
FIG. 2 is a perspective exploded view of the bone biopsy device of FIG. 1.

As depicted in FIG. 2, the handle assembly 110 may at least partially include a handle housing 111, a motor 122, a motor activation switch 124, a transmission 125, an inner cannula 150, and a penetrating member or trocar 160. The handle housing 111 can include an upper portion 112 and a grip portion 113. The grip portion 113 may be configured to be grasped by a hand of a practitioner during use of the bone biopsy device 100. The motor activation switch 124 may be disposed adjacent a distally facing surface of the grip portion 113 such that the motor activation switch 124 may be engageable by a finger of the practitioner. In other embodiments, the motor activation switch 124 may be disposed on any other suitable surface of the handle housing 111. The handle housing 111 may be formed of two separate halves that may be coupled using any suitable technique. For example, the separate halves may be coupled using a snap fit, welding, gluing, fasteners, pins, etc. The handle housing 111 may include any suitable polymeric and/or metallic material, such as polycarbonate, acrylonitrile butadiene styrene, polycarbonate/acrylonitrile butadiene styrene copolymer, nylon, acetal, polyethylene (e.g., such as high density polyethylene and/or low density polyethylene), silicone, thermoplastic elastomers, steel, stainless steel, aluminum, ceramic, and combinations thereof. The polymers may also be reinforced with other materials, such as glass or aramid fibers. The handle housing 111 may be formed using any suitable technique, such as injection molding, thermoforming, machining, 3D printing, etc.

The handle housing 111 can include a plurality of pockets or recesses configured to hold or retain at least some of the components of the handle assembly 110. For example, the handle housing 111 may include a power pack pocket 114 to retain the power pack 180, a motor pocket 115 to retain the motor 122, a transmission pocket 116 to retain the transmission 125, and an inner cannula pocket 121 to retain the inner cannula 150 and the trocar 160. In other embodiments, the handle housing 111 may include other pockets or recesses to hold or retain other components of the handle assembly 110.

In the depicted embodiment, the motor 122 may be disposed within the motor pocket 115 of the handle housing 111. The motor 122 may be any suitable type of rotatory motor. For example, the motor 122 may be a DC brushed motor, a DC brushless motor, a stepper motor, a servo motor, a pneumatic motor, or an AC powered motor, etc. The motor 122 may also be bi-directional. The motor 122 can include a drive shaft 123 extending from the motor 122. The motor 122 may rotate the drive shaft 123 at a speed ranging from about 0 rpm to about 50,000 rpm, or from about 15 rpm to about 20,000 rpm. The motor 122 can be electrically coupled to the power pack 180 and to the motor activation switch 124.

Figure 3A:
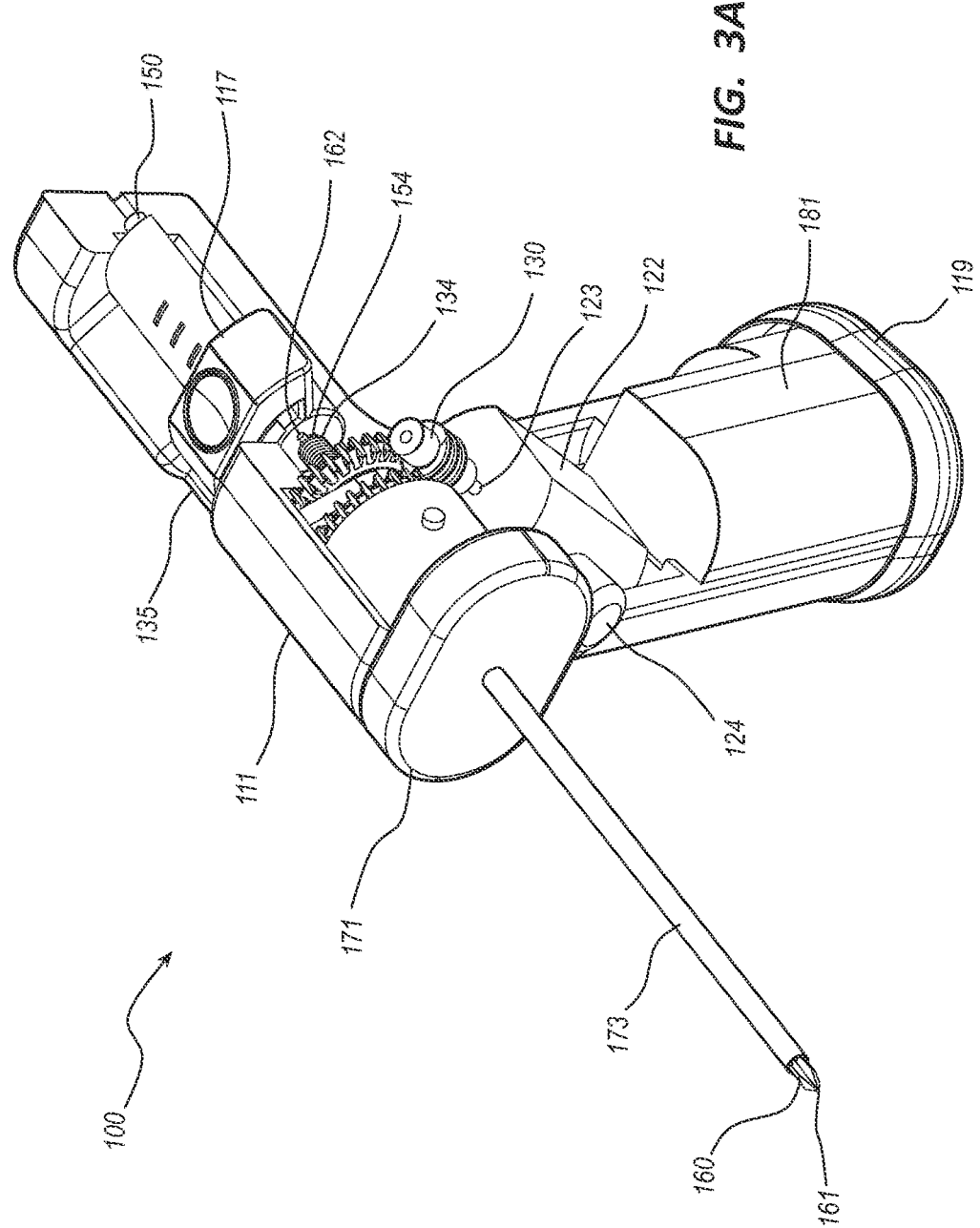
FIG. 3A is a perspective view of the bone biopsy device of FIG. 1 with a portion of a handle housing removed in a trocar extended configuration.
Figure 3B:
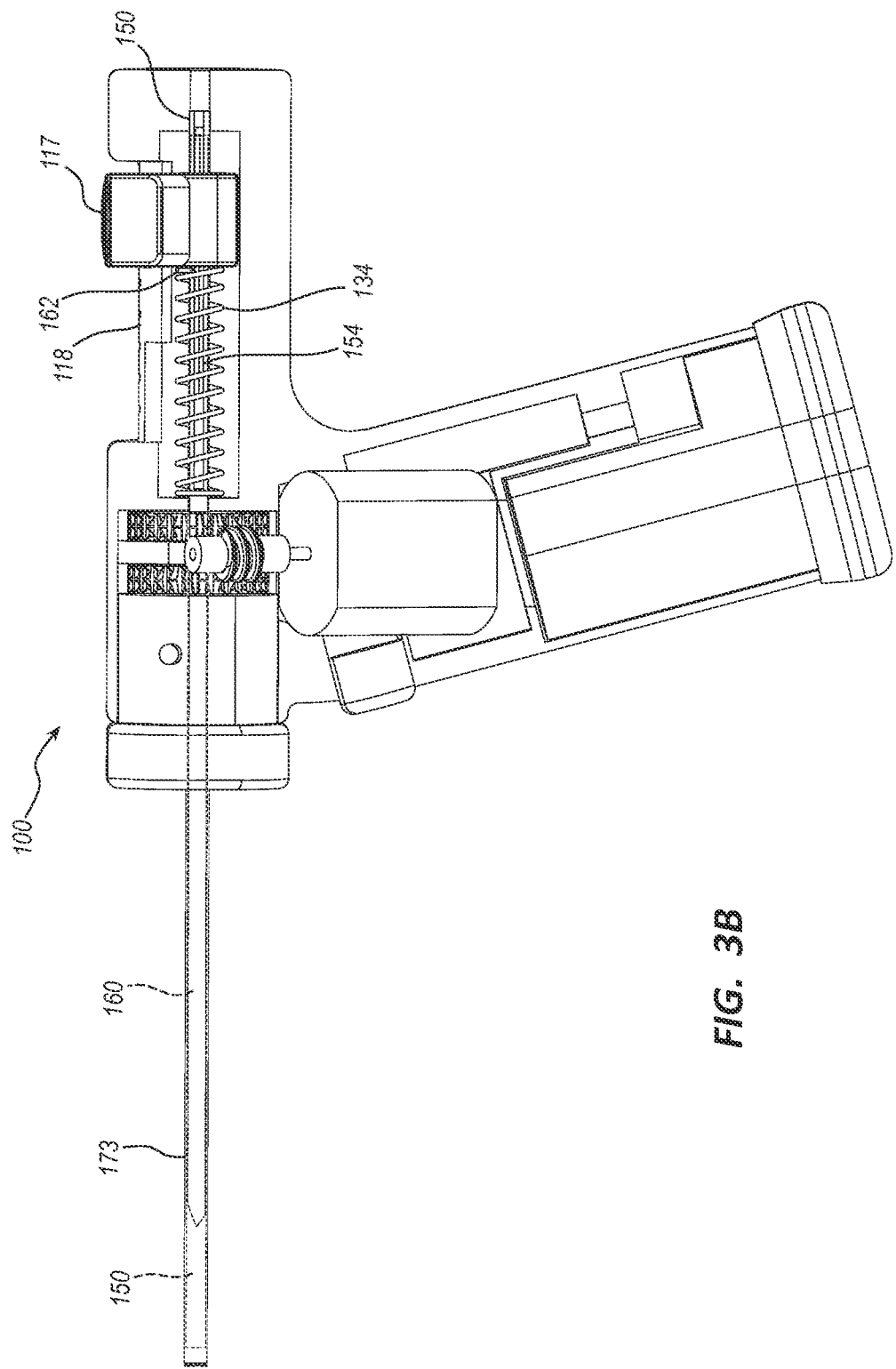
FIG. 3B is a side view of the bone biopsy device of FIG. 1 with a portion of the handle housing removed in a trocar retracted configuration.
Figure 4:
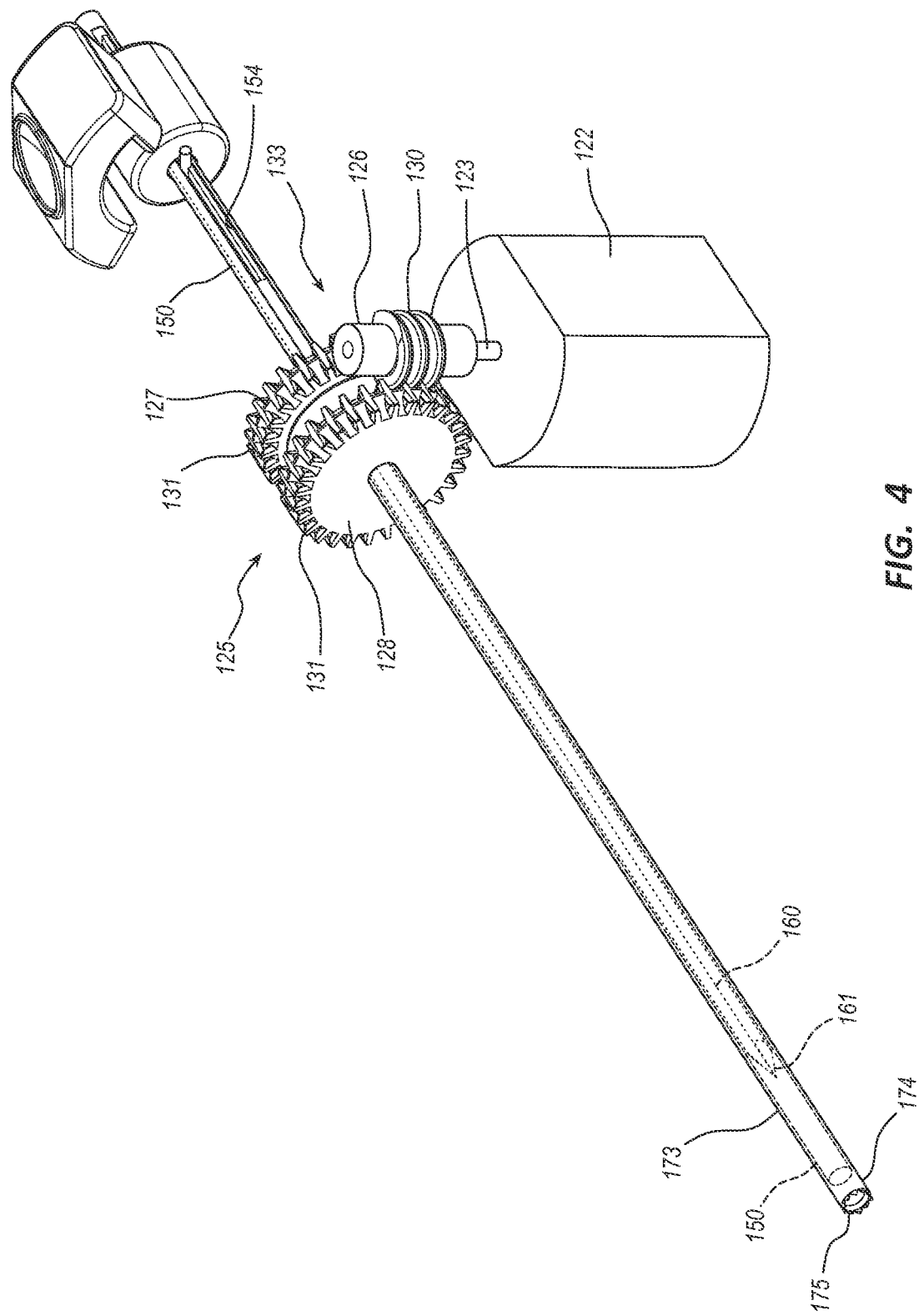
FIG. 4 is a perspective view of a transmission of the bone biopsy device of FIG. 1.

As illustrated in FIGS. 2-4, the transmission 125 can be disposed within the transmission pocket 116 of the handle housing 111. The transmission 125 can be operably coupled to the motor 122. In the illustrated embodiment, the transmission 125 includes a worm drive 133. The worm drive 133 may include a worm screw 126, a first worm gear 127, and a second worm gear 128. The worm screw 126 can be fixedly coupled to the drive shaft 123 and rotated by the motor 122. The worm screw 126 can include a spiral or helical thread 130 extending radially outward from the worm screw 126. The worm screw 126 may be oriented within a central vertical plane of the handle housing 111 and directed outwardly from a central vertical axis. The worm screw 126 may be formed from any suitable rigid or semi-rigid material, such as polycarbonate, acrylonitrile butadiene styrene, polycarbonate/acrylonitrile butadiene styrene copolymer, nylon, acetal, polyethylene (e.g., high density polyethylene and/or low density polyethylene), silicone, thermoplastic elastomer, steel, stainless steel, aluminum, ceramic, and combinations thereof. The polymers may be reinforced with other materials, such as glass or aramid fibers.

The worm screw 126 may operably couple with the first and second worm gears 127, 128. The first and second worm gears 127, 128 may be generally disk-shaped and include teeth 131 disposed around a periphery. The first and second worm gears 127, 128 may be oriented vertical to and may rotate about a horizontal axis of the bone biopsy device 100. The teeth 131 may be double beveled and may mesh with the helical thread 130 of the worm screw 126 such that when the motor 122 rotates the worm screw 126 the first and second worm gears 127, 128 rotate about the horizontal axis. The first and second worm gears 127, 128 may include a plurality of teeth 131 ranging in number from about 10 to about 100, from about 30 to about 80, or from about 25 to about 50. A gear reduction ratio of the transmission 125 may range from about 50:1 to about 20:1, or from about 40:1 to about 30:1.

In other words, a speed of rotation of the first and second worm gears 127, 128 may range from about 0 rpm to about 4000 rpm, from about 0 rpm to about 1000 rpm, from about 0 rpm to about 500 rpm, and from about 200 rpm to about 300 rpm. A delivered torque force may range from about 0.01 Nm to about 2 Nm, from about 0.5 Nm to about 1 Nm, and from about 0.5 Nm to about 0.75 Nm.

The first worm gear 127 can be rotatably coupled to the worm screw 126 and also continuously engaged with the worm screw 126 before, during, and after use. The first worm gear 127 may be fixedly coupled to the inner cannula 150 such that a proximal portion 151 extends proximally from the first worm gear 127 and a distal portion 152 extends distally from the first worm gear 127. The first worm gear 127 can rotate the inner cannula 150 about a longitudinal axis of the inner cannula 150 at the same speed as the first worm gear 127 is rotated about the horizontal axis. The second worm gear 128 may be fixedly coupled to an outer coax cannula 173 as will be described below.

The inner cannula 150, as depicted in the illustrated embodiment of FIG. 2, includes the proximal portion 151, the distal portion 152, and a lumen 153. The proximal portion 151 extends to a proximal end of and is rotatably coupled to the handle housing 111. The inner cannula 150 may be formed from any suitable material, such as stainless steel, titanium, titanium-nickel alloy, etc. A longitudinal slot 154 through a wall of the inner cannula 150 is disposed adjacent the proximal portion 151. In some embodiments, the longitudinal slot 154 may be reinforced. For example, a sleeve or tube including a slot may be disposed over the inner cannula 150 such that the slot of the sleeve aligns with the longitudinal slot 154. In another example, the first worm gear 127 may include a proximally extending member (e.g., sleeve or tube) that includes a slot such that the slot of the proximally extending member aligns with the longitudinal slot 154. In yet another embodiment, a distal end of the inner cannula 150 is fixedly coupled to the handle housing 111 distal to the first worm gear 127. The first worm gear 127 may include a proximally extending member (e.g., sleeve or tube) that includes a slot. The trocar 160 can be slidably disposed within the proximally extending member. The first worm gear eccentric shaft portion 127 may rotate the trocar 160 while the inner cannula 150 is rotationally stationary.

Figure 6A:
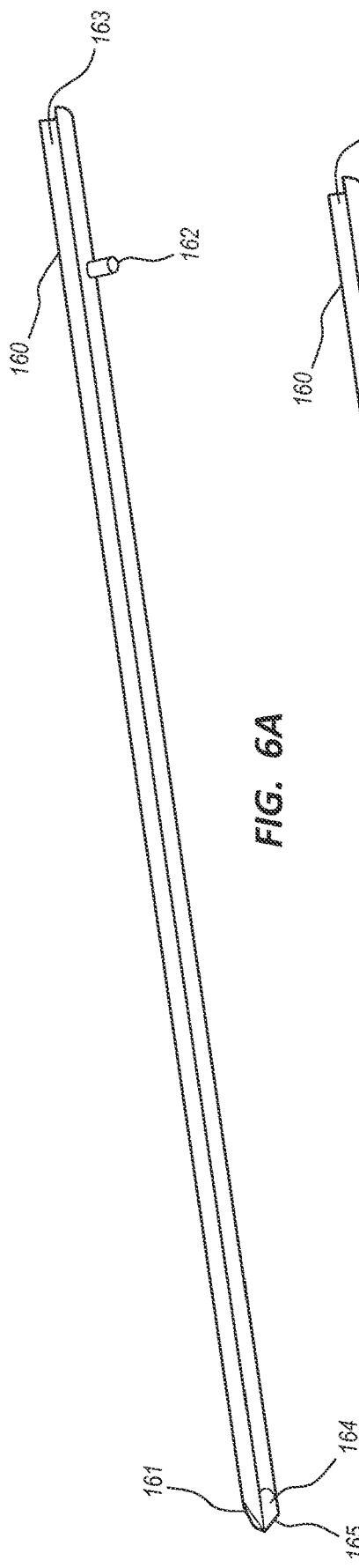
FIG. 6A is a perspective view of an embodiment of a trocar of the bone biopsy device of FIG. 1.
Figure 6B:
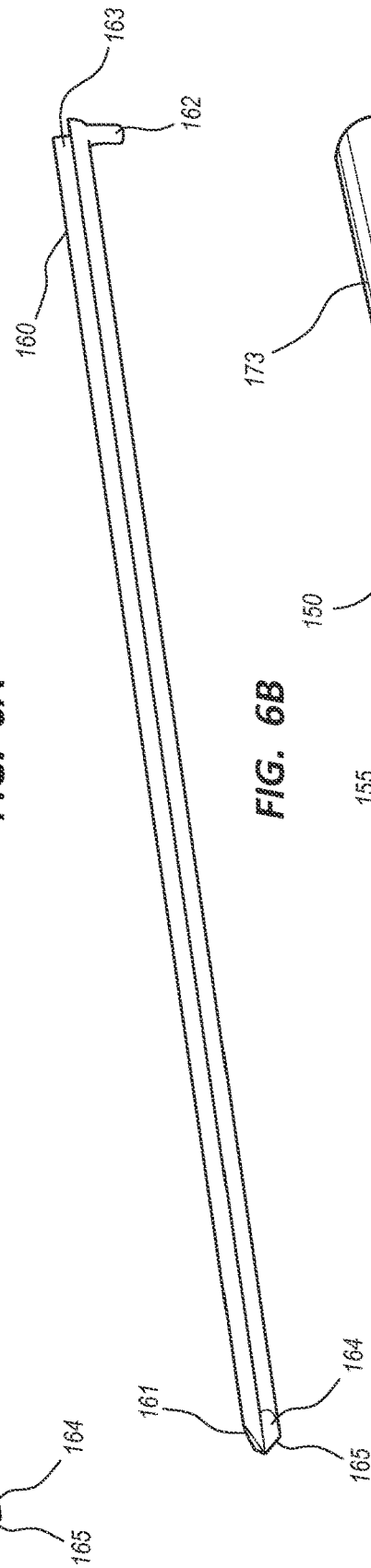
FIG. 6B is a perspective view of another embodiment of a trocar of the bone biopsy device of FIG. 1.
Figure 6C:
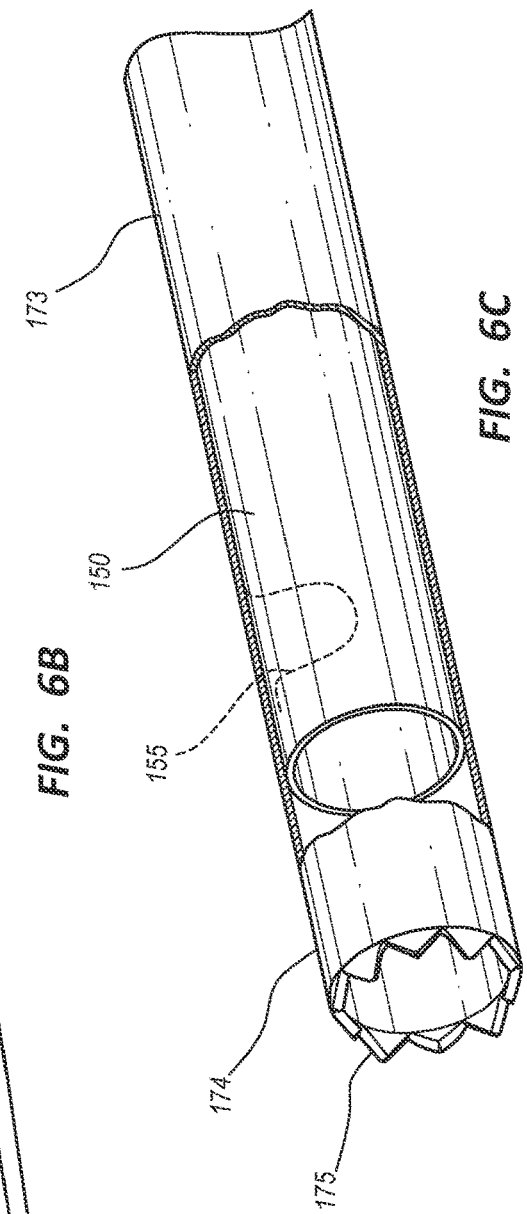
FIG. 6C is a cut-away perspective view of a part-off tab of an inner cannula of the bone biopsy device of FIG. 1.

In some embodiments, the inner cannula 150 may include a part-off tab 155 disposed within the lumen 153 adjacent the distal portion 152 as depicted in FIG. 6B. The part-off tab 155 may be actuatable from a non-actuated configuration where it is axially aligned with a longitudinal axis of the inner cannula 150 to an actuated configuration, as shown in FIG. 6B, where a portion of the part-off tab 155 extends radially inward into the lumen 153. The part-off tab 155 may be configured to sever a core tissue sample disposed within the lumen 153 from a bone lesion and/or bone marrow. A distal end of the part-off tab 155 may be fixedly coupled to a distal portion of the inner cannula 150. A proximal portion of the part-off tab 155 may be longitudinally translated such that a portion of the part-off tab is deflected inwardly. In other embodiments, other sampling/cutting mechanisms can also be used.

Referring again to FIGS. 2 and 6A-6B, the trocar 160, is slidingly disposed within the lumen 153 of the inner cannula 150. The trocar 160 may be an elongate rod having a penetrating tip 161. The penetrating tip 161 may include a plurality of facets 164 with cutting edges 165. The cutting edges 165 may be angled to allow for drilling of the trocar 160 into a bone. A laterally extending protrusion 162 may be disposed adjacent a proximal end of the trocar 160. In some embodiments the laterally extending protrusion 162 may be a pin as depicted in FIG. 6A. In other embodiments, a proximal end of the trocar 160 is bent at approximately a 90-degree angle relative to a longitudinal axis of the trocar 160 to form the lateral protrusion 162 as shown in FIG. 6B. The protrusion may be configured to extend through the longitudinal slot 154 of the inner cannula 150. The protrusion 162 may also be configured to engage with a slider member 117 to displace the trocar 160 relative to the inner cannula 150 from a retracted configuration to an extended configuration as depicted in FIGS. 3A and 3B. In the extended configuration the penetrating tip 161 extends distally beyond the inner cannula 150, and in the retracted position the penetrating tip 161 is disposed within the inner cannula 150. In certain embodiments, the trocar 160 may include a longitudinally extending groove or trough 163. The groove 163 may have a substantially V-shape and be configured for passage of a guidewire through the lumen 153 of the inner cannula 150.

As illustrated in FIGS. 2-4, the slider member 117 may be slidingly coupled to the handle housing 111. The slider member 117 may also be sliding coupled to the inner cannula 150. The protrusion 162 is shown to extend through the slot 154 and is disposed distal to the slider member 117. When the slider member 117 is displaced from a proximal position to a distal position, as shown in FIG. 3, the slider member 117 engages the protrusion 162 to displace the trocar 160 from the retracted configuration to the extended configuration. The slider member 117 may be locked in the distal position when engaged with a locking member 135 of the handle housing 111. When the slider member 117 is locked in the distal position, the trocar 160 is also locked in the extended configuration. A resilient member or compression spring 134 may be disposed distal to the protrusion 162 and the slider member 117. The resilient member 134 can be compressed when the slider member 117 is displaced to the distal position. When the slider member 117 is unlocked from the distal position, the resilient member 134 may decompress and apply a proximally directed force to the protrusion 162 and the slider member 117 to displace the slider member 117 to the proximal position and the trocar 160 to the retracted configuration. The resilient member 134 may bias the slider member 117 to the proximal position.

In the illustrated embodiment of FIG. 2, the handle housing 111 also includes a core tissue sample length scale 118 disposed adjacent the slider member 117. The scale 118 may include a plurality of indices, e.g., lines, spaced equidistance apart. In some embodiments, a distance between the lines may be 0.5 mm, one millimeter, two millimeters, five millimeters, 10 millimeters, etc. The scale 118, in cooperation with the slider member 117, may be used to determine a length of a core tissue sample that is contained within the lumen 153 of the inner cannula 150. For example, the slider member 117 and the trocar 160 may be displaced distally until the penetrating tip 161 engages with the core tissue sample and the practitioner feels increased resistance to displace the slider member 117. A portion of the slider member 117 may be adjacent to one line of the scale 118 that correlates with a length of the core tissue sample.

As depicted in the illustrated embodiment of FIGS. 2 and 5A, the coax assembly 170 may be selectively coupled to the handle assembly 110. The coax assembly 170 may include the second worm gear 128, a coax connector 171, and an outer coax cannula 173. The coax connector 171 may include a coupling member 172 configured to mate with a receiving member 120 of the handle assembly 110. For example, coax connector 171 and the handle assembly 171 may be coupled together using a bayonet mount. The coupling member 172 may be a laterally extended protrusion sized to be received by a channel of the receiving member 120. The channel of the receiving member 120 may be substantially L-shaped such that the protrusion is proximally inserted into the channel and then rotated to lock the handle assembly 110 and the coax assembly 170 together. When the coax assembly 170 is selectively removed from the handle assembly 110, the coax connector 171 and coupling member 172 are rotated in an opposite direction than when locking and displaced distally. Other types of coupling mechanisms may be contemplated and are within the scope of this disclosure.

The outer coax cannula 173 extends distally from the worm gear 128 and is rotatably coupled to the coax connector 171. In other words, the outer coax cannula 173 is rotatable relative to the coax connector 171. The coax connector 171 can also be coupled such that it does not translate longitudinally (e.g., distally and/or proximally) on the outer coax cannula 173. The inner cannula 150 is coaxially disposed within a lumen 176 of the outer coax cannula 173. The inner cannula 150 may not extend distally beyond the outer coax cannula 173. The outer coax cannula 173 may include a cutting tip, such as a trephine tip 174 having a plurality of teeth 175 configured to rotate and saw a hole into a bone lesion and/or bone marrow when the outer coax cannula 173 is rotated. In some embodiments, the teeth 175 may be in alignment with a longitudinal axis of the outer coax cannula 173. In other embodiments, the teeth 175 may be alternatingly biased inward and outward relative to the longitudinal axis. In the illustrated embodiment, a depth limiting member 177 is slidably coupled to the outer coax cannula 173. The depth limiting member 177 may be used to indicate an insertion depth of the outer coax cannula 173 into the patient that may correlate to a core tissue sample length. In some embodiments, the outer coax cannula 173 may be rotatable relative to the depth limiting member 177. In this embodiment, the depth limiting member 177 may be held by a user while the outer coax cannula 173 is rotating to guide the outer coax cannula 173 into the patient.

A proximal end of the outer coax cannula 173 can extend proximally from the coax connector 171. The second worm gear 128 may be fixedly coupled to the proximal end. When the coax assembly 170 is coupled to the handle assembly 110, the second worm gear 128 engages with the worm screw 126 such that the motor 122 rotates the second worm gear 128 and the outer coax cannula 173 at the same speed as the inner cannula 150 and the trocar 160 are rotated. In other embodiments, the rotation speed of the outer coax cannula 173 may be different, e.g., either faster or slower, than the rotation speed of the inner cannula 150 and the trocar 160. In still other embodiments, the rotation direction of the outer coax cannula pin passages 173 may be different than the rotation direction of the inner cannula 150 and the trocar 160.

As depicted in the illustrated embodiment of FIG. 2, the power pack 180 is selectively removably disposed within a power pack pocket 114 of the grip portion 113 of the handle housing 111. A removable cap 119 may retain the power pack 180 within the handle housing 111. The power pack 180 may include a case 181 containing a power source 182, a controller 183, and a connector 184. The power source 182 may include a single battery or a plurality of batteries. The battery or batteries may be replaceable or rechargeable. The controller 183 may include a printed circuit board that is electrically coupled to the power source 182, the motor 122, and the motor activation switch 124. The controller 183 can be configured to control activation and speed of the motor 122 when the motor activation switch 124 is actuated by the practitioner. The connector 184 may selectively electrically couple the power pack 180 to the handle assembly 110. Following a bone biopsy procedure, the power pack 180 may be selectively removed from the bone biopsy device 100. The handle assembly 110 and outer coax assembly 170 can be disposed of. As previously mentioned, the motor 122 can also be selectively removed from the handle assembly 110 if desired. When removed, the power pack 180 and/or motor 122 may be refurbished for use in a subsequent procedure. Refurbishment may include cleaning, sterilizing, recharging or replacing the power source 182 and/or motor 122, etc. Alternatively, the power pack 180 (and/or motor 122) may be disposed of in an environmentally friendly manner. The bone biopsy device 100 may be disposed of following standard procedures for disposal of a medical device.

In use, the bone biopsy device 100 can be used to obtain a core tissue sample from a bone lesion and/or bone marrow. The power pack 180 can be inserted into the handle assembly 110. The cap 119 can be coupled to the handle assembly 110 to retain the power pack 180 within the handle assembly 110 and to prevent contamination of the power pack 180 with body fluids. The coax assembly 170 may be coupled to the handle assembly 110. The slider member 117 can be displaced distally and locked in the distal position such that the trocar 160 is displaced from the retracted configuration to the extended configuration. In the extended configuration, the penetrating tip 161 extends distally beyond the outer coax cannula 173.

Figure 7A:
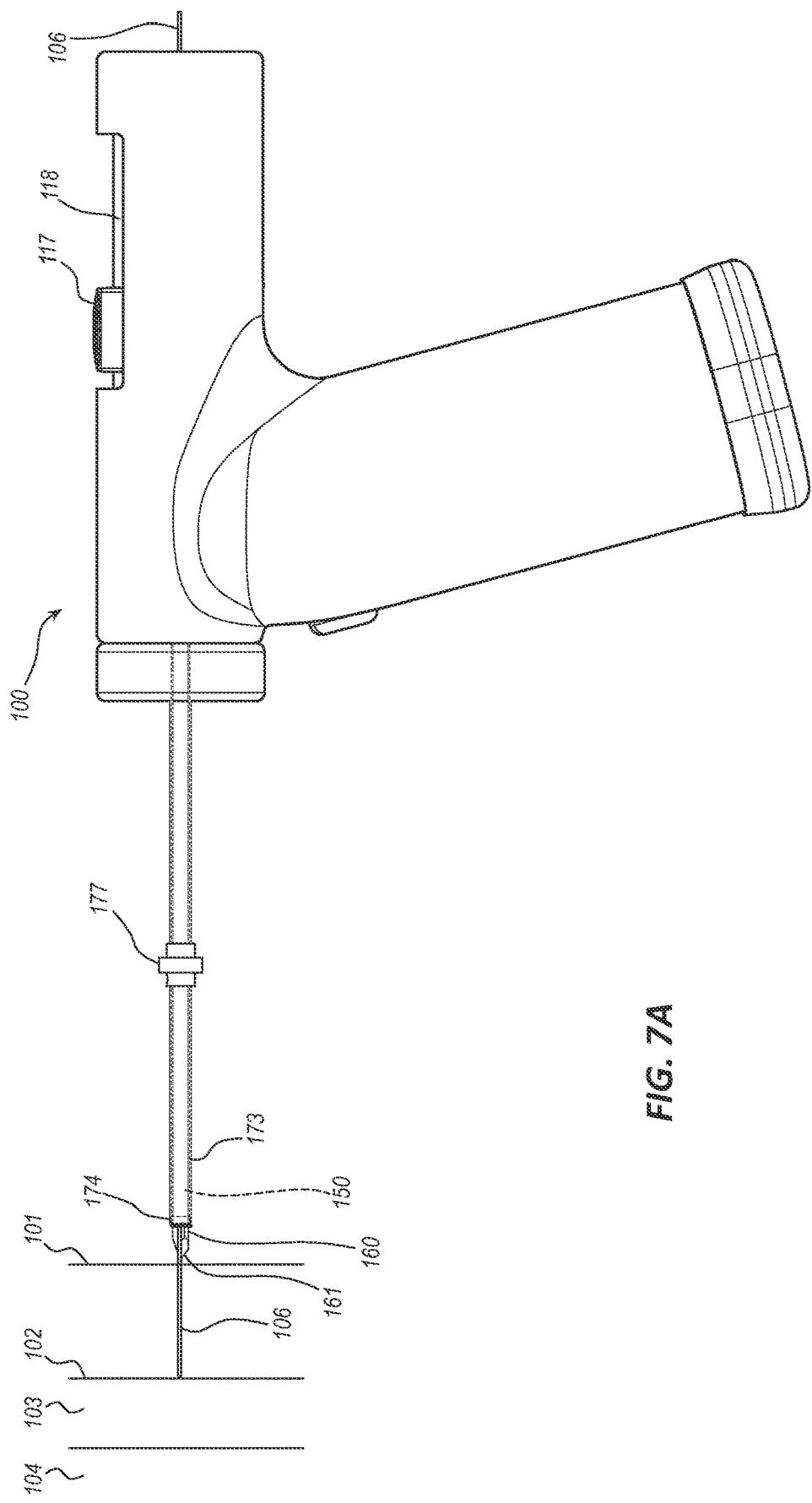
FIG. 7A is a side view of the bone biopsy device of FIG. 1 inserted into skin over a guidewire.

As depicted in FIG. 7A, in certain instances, the trocar 160 may be optionally inserted into the patient over a guidewire 106 that passes through the inner cannula 150 via the trocar groove 163. The guidewire 106 can then be removed prior to rotating the outer coax cannula 173, the inner cannula 150, and trocar 160. In other instances, rotation of the outer coax cannula 173, the inner cannula 150, and the trocar 160 can begin prior to removal of the guidewire 106. For example, rotation of the outer coax cannula 173, the inner cannula 150, and the trocar 160 and engagement into the bone can be initiated, after which the guidewire 106 can be removed.

Figure 7B:
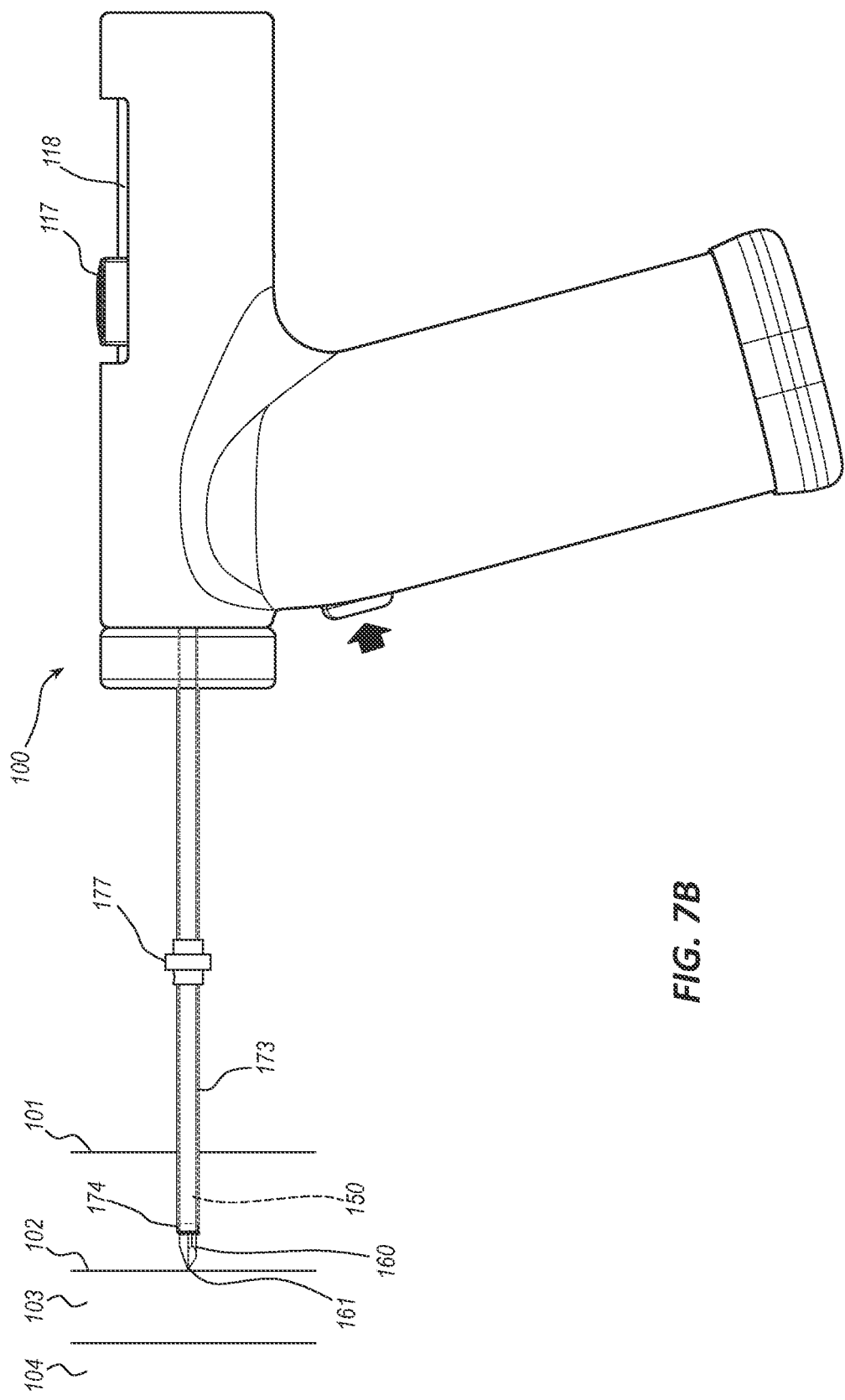
FIG. 7B is a side view of the bone biopsy device of FIG. 1 inserted in a bone.

As depicted in FIG. 7B, the trocar 160, the inner cannula 150, and the outer coax cannula 173 can be inserted through the patient's skin 101 as a unit until the penetrating tip 161 is adjacent a bone 102 (optionally with a guide wire if desired). The trocar 160 is in the extended configuration and the slider member 117 is locked in the distal position.

Figure 7C:
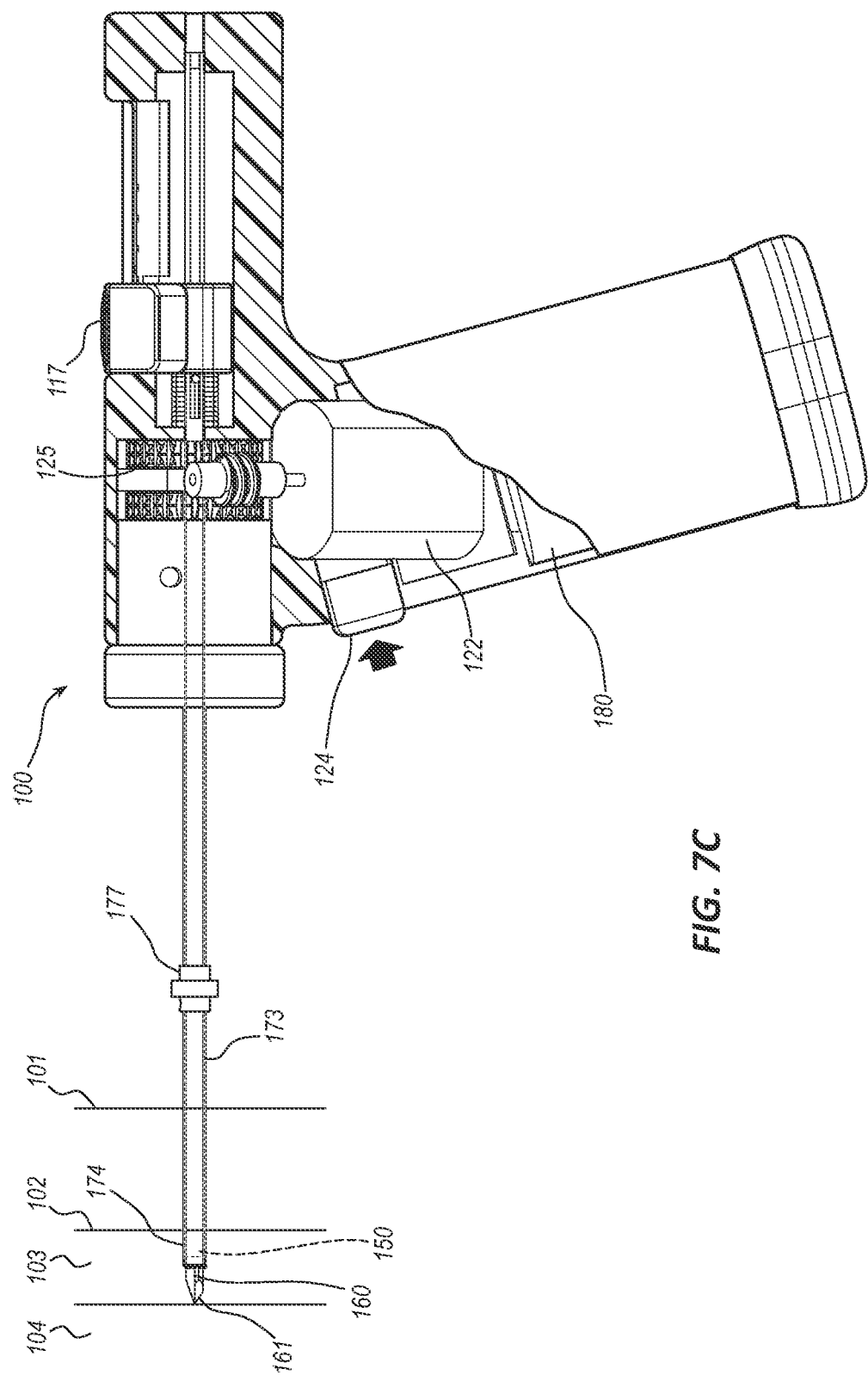
FIG. 7C is a side view of the bone biopsy device of FIG. 1 drilled through a cortical bone layer.

FIG. 7C illustrates the trocar 160 drilled through the cortical layer 103 of the bone 102. To drill the trocar 160 through the cortical layer 103 of the bone 102, the motor 122 can be activated when the motor activation switch 124 is actuated by the practitioner. In some embodiments, the practitioner can control the motor speed through the motor activation switch 124. For example, the practitioner may partially actuate the motor activation switch 124 to run the motor 122 at a first speed and fully actuate the motor activation switch 124 to run the motor 122 at a second speed, third speed, fourth speed. etc. The motor 122 can rotate the transmission 125 to rotate the trocar 160 to drill through the cortical layer 103 of the bone 102 until the cutting tip 174 of the outer coax cannula 173 is adjacent a bone lesion and/or bone marrow 104. In certain embodiments, the depth limiting member 177 may be positioned on the outer coax cannula 173 to limit an insertion depth to a desired core tissue sample length.

Figure 7D:
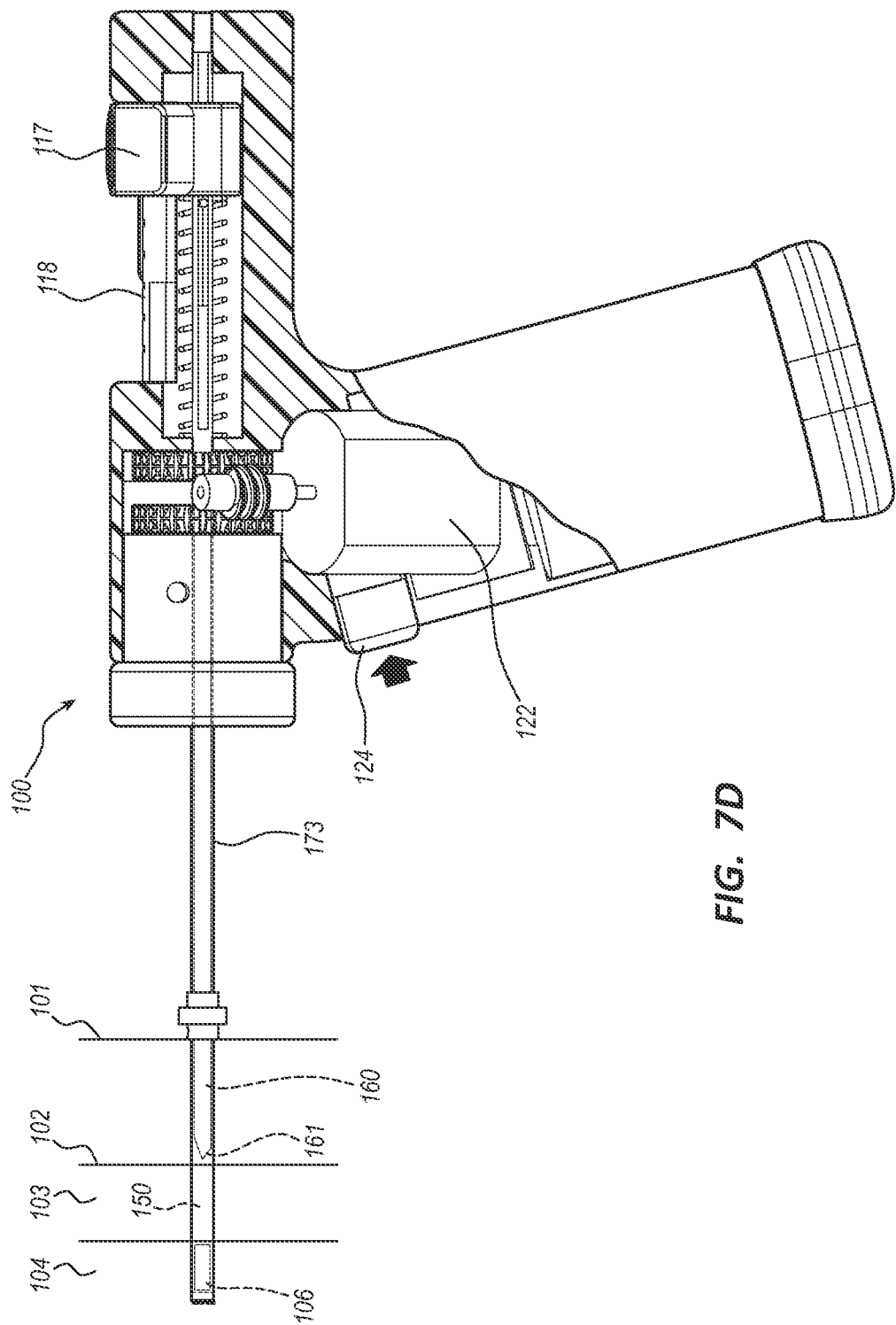
FIG. 7D is a side view of the bone biopsy device of FIG. 1 drilled into a bone lesion and/or bone marrow.

FIG. 7D illustrates the slider member 117 unlocked and displaced to the proximal position. The trocar 160 is displaced from the extended configuration to the retracted configuration. The motor 122 may be activated to rotate the outer coax cannula 173, the inner cannula 150, and the trocar 160. The cutting tip 174 of the outer coax cannula 173 may saw a hole into the bone lesion and/or bone marrow 104. A core tissue sample 106 may be disposed within the inner cannula 150 as the cutting tip 174 saws the hole into the bone lesion and/or bone marrow 104. In certain embodiments, a part-off tab 155 or other sampling mechanism (not shown) may be actuated while the inner cannula 150 is rotating or stationary to sever the core tissue sample 106 from the bone lesion and/or bone marrow 104. The direction of rotation can also be reversed to sever the core tissue sample 106. In some embodiments, the core tissue sample length scale 118 may be used to determine a length of the core tissue sample 106 disposed within the inner cannula 150 by distally displacing the slider member 117 and the trocar 160 until the penetrating tip 161 engages with the core tissue sample 106 and resistance to distal movement of the slider member 117 is sensed by the practitioner. A portion of the slider member 117 may correspond to an indicium of the core tissue sample length scale 118 to indicate the length of the core tissue sample 106.

FIG. 7E depicts the coax assembly 170 decoupled from the handle assembly 110. The inner cannula 150 and the trocar 160 are removed from the outer coax cannula 173. The outer coax cannula 173 may be left in the patient for obtaining subsequent core tissue samples and or biopsy samples. In other embodiments, the coax assembly 170 may not be decoupled from the handle assembly 110 and the outer coax cannula 173 may be removed from the patient.

FIG. 7F illustrates the core tissue sample 106 ejected from the inner cannula 150 when the slider member 117 is displaced from the proximal position to the distal position and the trocar 160 is displaced from the retracted configuration to the extended configuration. As the trocar 160 is displaced to the extended position, the penetrating tip 161 may push against the core tissue sample 106 to displace it distally from the inner cannula 150.

Figure 7G:
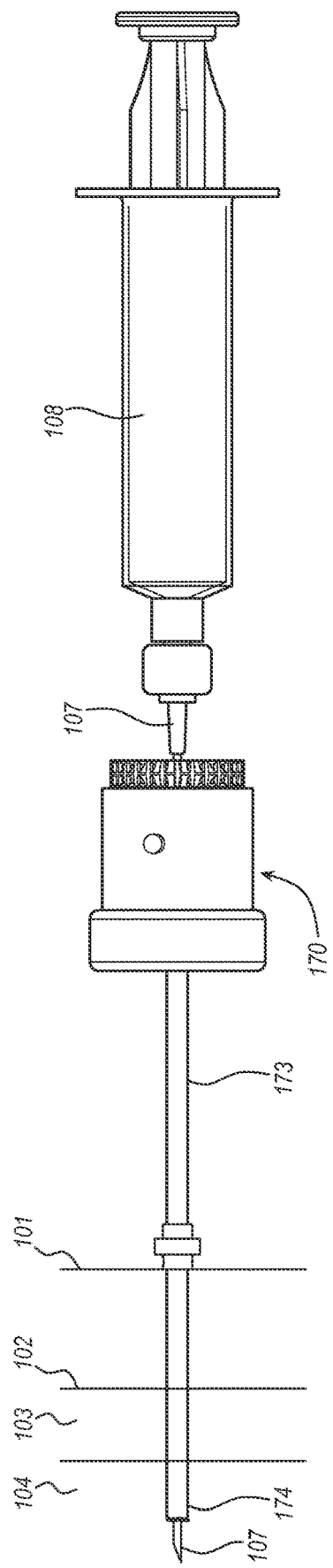
FIG. 7G is a side view of the bone biopsy device of FIG. 1 with the inner cannula removed from an outer coax cannula and an aspiration needle inserted through the coax cannula.

In some instances, as depicted in FIG. 7G, an aspiration needle 107 and aspiration device (e.g., syringe, vacuum sample collection tube, or pump, etc.) 108 may be used to obtain a core tissue sample 106 of the bone marrow 104. For example, the needle may be inserted into the bone marrow 104 through the outer coax cannula 173 (which can be seated in the bone and/or patient after being decoupled from the handle assembly 110). The aspiration device 108 can then be used to aspirate a tissue sample of the bone marrow 104 through the needle.

Figure 8:
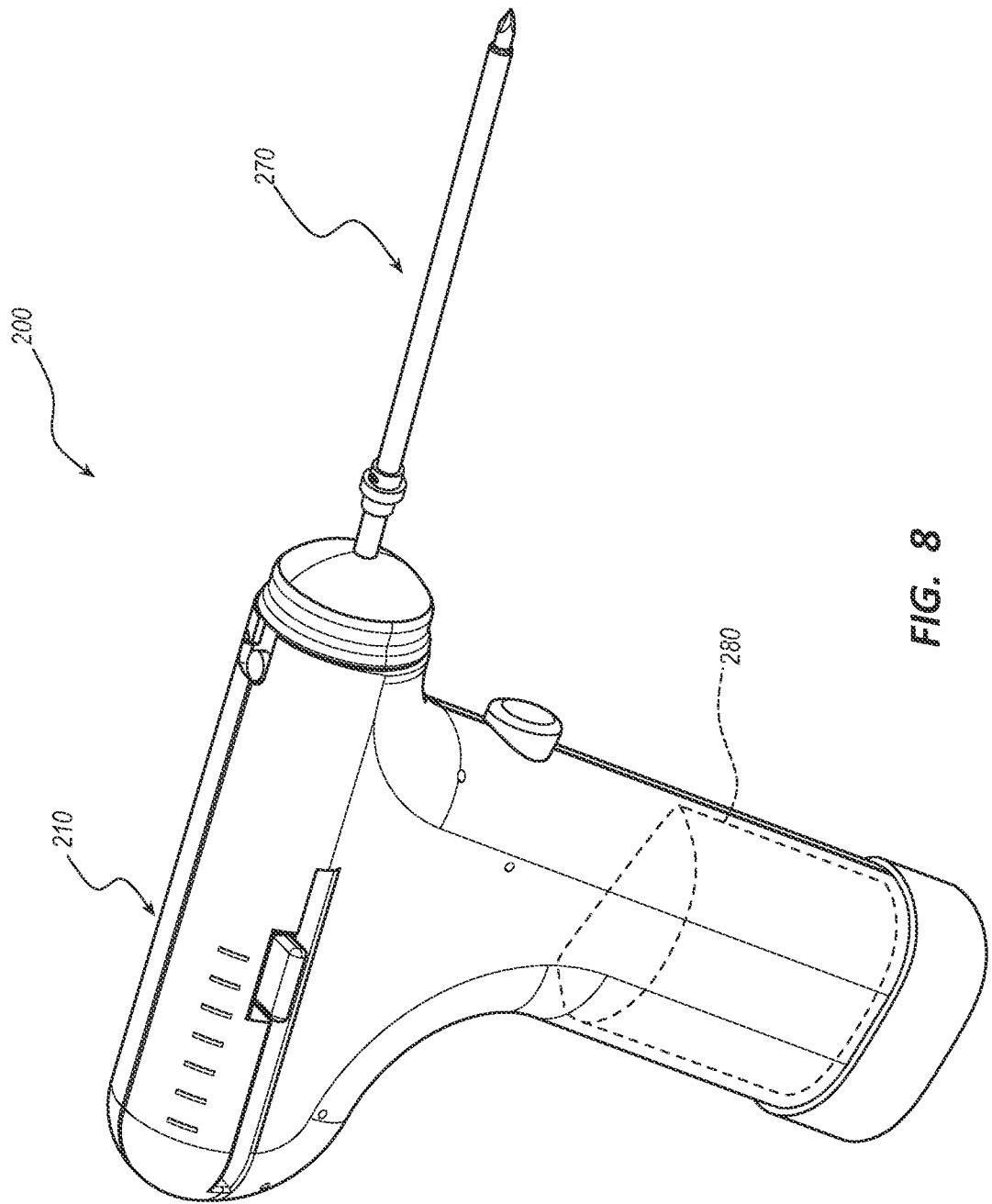
FIG. 8 is a perspective view of another embodiment of a bone biopsy device.
Figure 9:
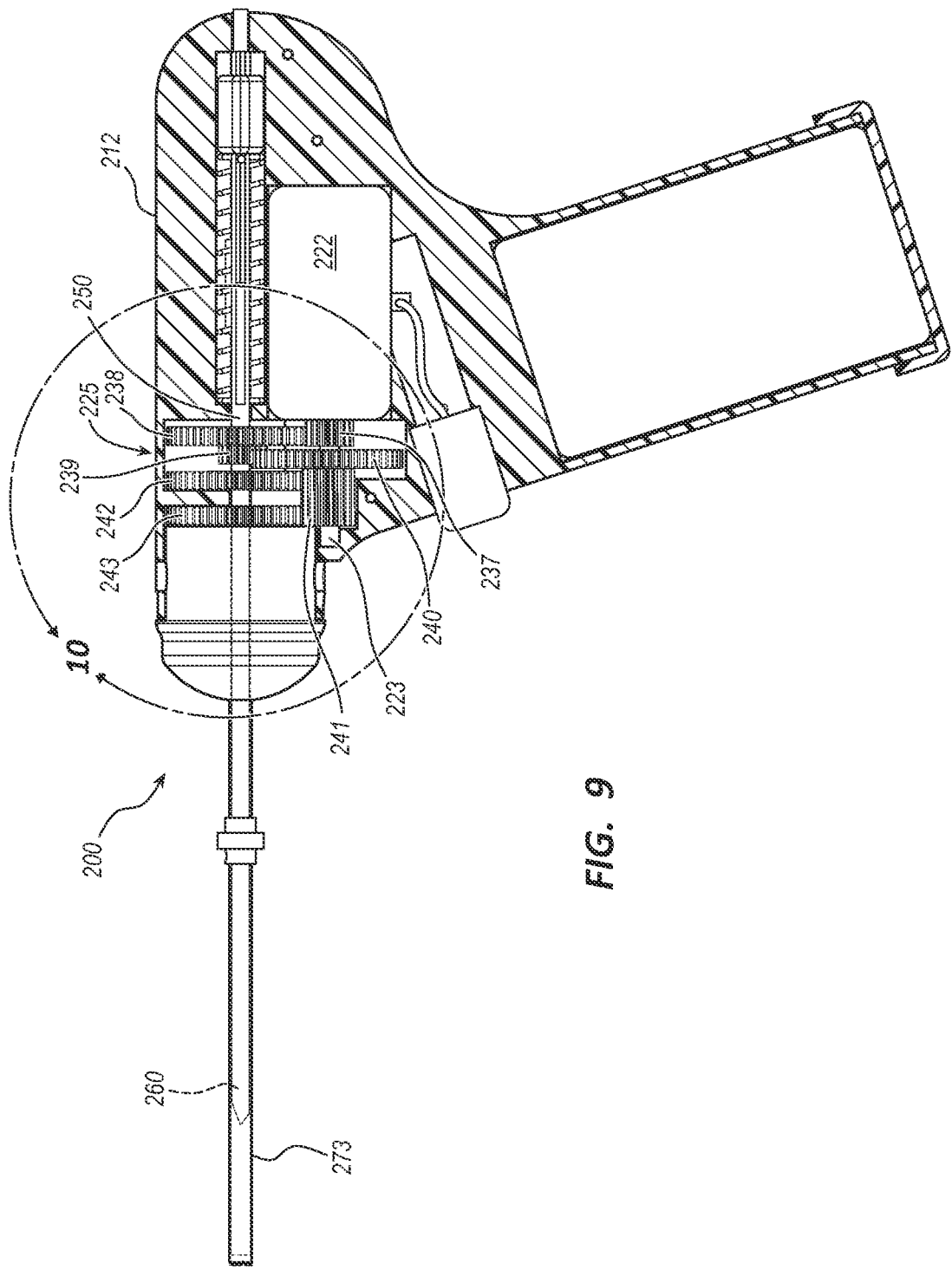
FIG. 9 is a side cut-away view of the bone biopsy device of FIG. 8.
Figure 10:
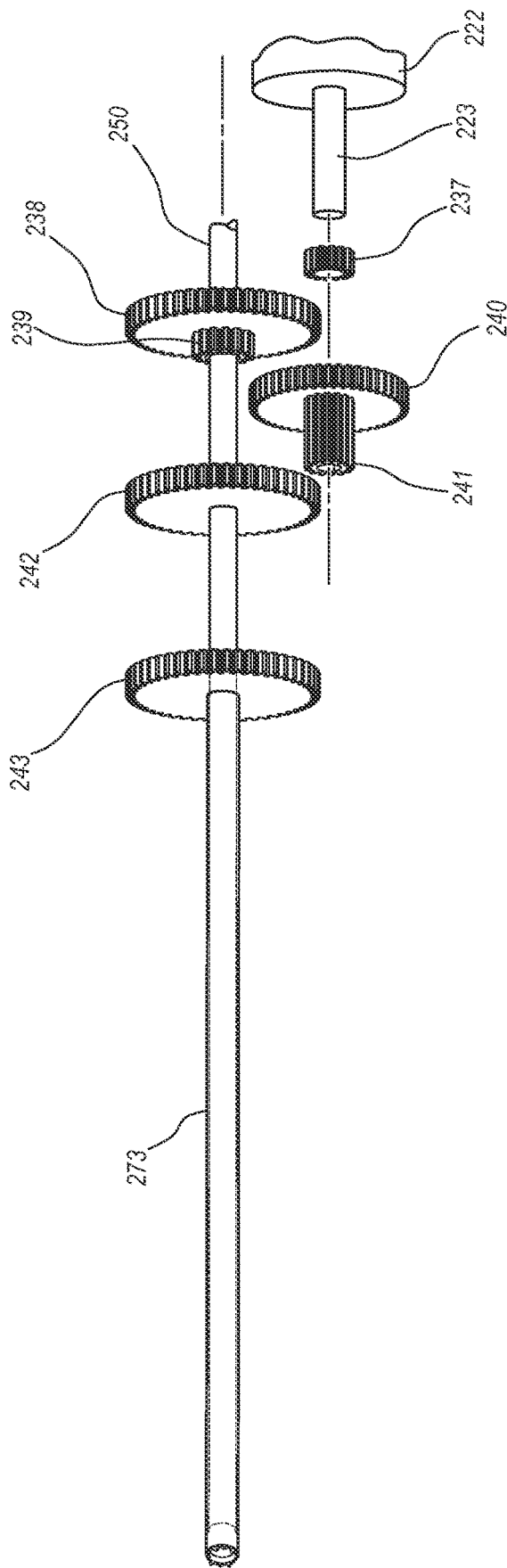
FIG. 10 is an exploded view of a transmission of the bone biopsy device of FIG. 8.

FIGS. 8-10 depict an embodiment of a bone biopsy device 200 that resembles the bone biopsy device 100 described above in certain respects. Accordingly, like features are designated with like reference numerals, with the leading digit incremented to "2." For example, the embodiment depicted in FIGS. 8-10 includes a handle assembly 210 that may, in some respects, resemble the handle assembly 110 of FIG. 1. Relevant disclosure set forth above regarding similarly identified features thus may not be repeated hereafter. Moreover, specific features of the handle assembly 110 and related components shown in FIGS. 1-7G may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the bone biopsy device 200 and related components depicted in FIGS. 8-10. Any suitable combination of the features, and variations of the same, described with respect to the bone biopsy device 100 and related components illustrated in FIGS. 1-7G can be employed with the bone biopsy device 200 and related components of FIGS. 8-10, and vice versa. This pattern of disclosure applies equally to further embodiments depicted in subsequent figures and described hereafter, wherein the leading digits may be further incremented.

FIGS. 8-10 illustrate another embodiment of a bone biopsy device 200. The bone biopsy device 200 can include a handle assembly 210, a coax assembly 270, and a power pack 280. The handle assembly 210 may include a motor 222 and a transmission 225. As depicted in FIG. 9, the motor 222 is oriented parallel to a horizontal axis of a handle housing 212. The motor 222 includes a drive shaft 223 extending distally from the motor 222.

As shown in FIGS. 9-10, the transmission 225 may include a plurality of spur gears configured to provide a plurality of gear reductions and to rotate an inner cannula 250, a trocar 260, and an outer coax cannula 273. FIGS. 9-10 depict a first spur gear 237 that is fixedly coupled to the drive shaft 223. A second spur gear 238 is radially offset from and engages the first spur gear 237. The second spur gear 238 may be configured to rotate freely around the inner cannula 250. The engagement of the first spur gear 237 and the second spur gear 238 may provide a first gear reduction.

A third spur gear 239 may be fixedly coupled to the second spur gear 238 and be configured to rotate freely around the inner cannula 250 with the second spur gear 238. A fourth spur gear 240 may be disposed adjacent the first spur gear 237 on the drive shaft 223 and be configured to engage with the third spur gear 239. The fourth spur gear 240 may be configured to rotate freely around the drive shaft 223. The engagement of the fourth spur gear 240 and the third spur gear 239 may provide a second gear reduction. A fifth spur gear 241 may be fixedly coupled to the fourth spur gear 240 and be configured to rotate freely around the drive shaft 223. A length of the fifth spur gear 241 may be longer than a length of the first spur gear 237 such that the fifth spur gear 241 can engage with a sixth and a seventh spur gear 242, 243.

The sixth spur gear 242 can be disposed adjacent the third spur gear 239 and can be fixedly coupled to the inner cannula 250 such that rotation of the sixth spur gear 242 causes rotation of the inner cannula 250 and the trocar 260. The sixth spur gear 242 may be configured to engage with the fifth spur gear 241 and may provide a third gear reduction. The seventh spur gear 243 can be disposed adjacent the sixth spur gear 242 and can be fixedly coupled to the outer coax cannula 273 such that rotation of the seventh spur gear 243 causes rotation of the outer coax cannula 273. The seventh spur gear 243 may be configured to engage with the fifth spur gear 241 and may provide a fourth gear reduction.

In certain embodiments, an overall gear reduction ratio from the first spur gear 237 to the sixth and seventh spur gears 242, 243 may range from about 50:1 to about 20:1, or from about 40:1 to about 30:1. Thus, a rotation speed of the inner cannula 250, the trocar 260, and the outer coax cannula 273 may range from about 0 rpm to about 4,000 rpm, from about 0 rpm to about 1000 rpm, from about 0 rpm to about 500 rpm and from about 200 rpm to about 300 rpm.

Use of the biopsy device 200 can be similar to the biopsy device 100 previously discussed. For example, a trocar can be extended to facilitate insertion of an outer coax cannula and inner cannula into the skin of a patient. The trocar may be rotated by a motor to drill through the cortical layer of the bone. The outer coax cannula and the inner cannula can be rotated by the motor to saw a hole into the bone lesion and/or bone marrow and collect a core tissue sample within the inner cannula. The inner cannula and the trocar may be removed from the outer coax cannula. The trocar can then be extended to eject the core tissue sample from the inner cannula.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A bone biopsy device, comprising:
a handle assembly, comprising:
a handle housing comprising a grip portion and an upper portion;
a motor;
a motor activation switch;
a transmission operably coupled to the motor;
an inner cannula, wherein the motor is offset from a longitudinal axis of the inner cannula; and
a penetration member; and
a coax assembly, comprising:
an outer coax cannula,
wherein the inner cannula comprises a proximal portion, a distal portion, and a lumen extending through a length of the inner cannula, and wherein the inner cannula extends into the upper portion of the handle housing such that the proximal portion is disposed within the handle housing and the distal portion extends distally from the handle housing,
wherein the upper portion of the handle housing comprises a proximal end region and a distal end region, the proximal end region including an opening,
wherein the penetration member comprises a groove extending from a proximal end to a distal end of the penetration member, and
wherein the opening in the proximal end region of the upper portion of the handle housing, the inner cannula, and the penetration member are positioned for passage of a guidewire through the opening, the lumen of the inner cannula, and the groove.

2. The bone biopsy device of claim 1, wherein the inner cannula is disposed at least partially within the upper portion of the handle housing and the motor is disposed at least partially within the grip portion of the handle housing.

3. The bone biopsy device of claim 1, wherein the transmission comprises a plurality of spur gears.

4. The bone biopsy device of claim 3, wherein the plurality of spur gears comprises:
a first spur gear coupled to a drive shaft of the motor and rotated by the motor;
a second spur gear rotatably coupled to the inner cannula, wherein the second spur gear is engaged with and rotated by the first spur gear.

5. The bone biopsy device of claim 1, wherein the transmission further comprises a gear reduction member.

6. The bone biopsy device of claim 5, wherein a total gear reduction ratio of the bone biopsy device ranges from 50:1 to 20:1.

7. The bone biopsy device of claim 1, wherein the penetration member is slidably disposed within the lumen of the inner cannula.

8. The bone biopsy device of claim 1, wherein the handle assembly comprises a slider member, wherein the slider member engages the penetration member to longitudinally displace the penetration member from a retracted configuration to an extended configuration.

9. The bone biopsy device of claim 1, wherein the coax assembly further comprises a coax connector to selectively couple the coax assembly to the handle assembly.

10. The bone biopsy device of claim 1, wherein the transmission includes a worm drive comprising a first worm gear, a second worm gear, and a worm screw operably coupled with the first worm gear and the second worm gear, wherein the first worm gear and the second worm gear rotate responsive to rotation of the worm screw by the motor.

11. The bone biopsy device of claim 1, further comprising:
a power pack comprising a power source.

12. A bone biopsy device, comprising:
a handle assembly, comprising:
a proximal end region having an opening;
a distal end region;
a motor;
a transmission comprising a gear reduction member and a plurality of spur gears;
an inner cannula positioned at least partially within the handle assembly and extending from the distal end region of the handle assembly, wherein the inner cannula is positioned to receive a guidewire extending through the opening in the proximal end region of the handle assembly; and
a penetration member slidably disposed in a lumen of the inner cannula; and
a coax assembly, comprising:
an outer coax cannula,
wherein the handle assembly comprises a slider member, wherein the slider member engages the penetration member to longitudinally displace the penetration member from a retracted configuration to an extended configuration.

13. The bone biopsy device of claim 12, wherein the motor is offset from a longitudinal axis of the inner cannula.

14. The bone biopsy device of claim 12, wherein the penetration member comprises a groove extending from a proximal end to a distal end of the penetration member, wherein the groove is positioned to receive the guidewire extending through the opening in the proximal end region and through the inner cannula.

15. The bone biopsy device of claim 12, wherein the coax assembly further comprises a coax connector to selectively couple the coax assembly to the handle assembly.

16. A method of obtaining a core tissue sample from a patient, comprising:
obtaining a bone biopsy device, comprising:
a handle assembly, wherein the handle assembly comprises:
a motor;
a transmission operably coupled to the motor;
an inner cannula, wherein the motor is offset from a longitudinal axis of the inner cannula; and
a penetration member; and
a coax assembly, wherein the coax assembly comprises an outer coax cannula;
advancing the bone biopsy device over a guidewire, the guidewire extending through an opening in a proximal end region of the handle assembly and through the inner cannula;
inserting the outer coax cannula, the inner cannula, and the penetration member into the patient;
retracting the penetration member from an extended configuration to a retracted configuration;
inserting the inner cannula into a bone lesion and/or bone marrow;
obtaining the core tissue sample within the inner cannula;
removing the inner cannula from the patient; and
displacing the penetration member from the retracted configuration to the extended configuration to eject the core tissue sample from the inner cannula.

17. The method of claim 16, further comprising inserting the inner cannula and the penetration member into the patient through the outer coax cannula.

18. The method of claim 16, further comprising inserting a needle into the patient through the outer coax cannula and aspirating a tissue sample.

19. The method of claim 16, further comprising positioning a depth limiting member at a location on the outer coax cannula.

20. A bone biopsy device, comprising:
a handle assembly, comprising:
a motor;
a transmission operably coupled to the motor, wherein the transmission includes a worm drive comprising a first worm gear, a second worm gear, and a worm screw operably coupled with the first worm gear and the second worm gear, wherein the first worm gear and the second worm gear rotate responsive to rotation of the worm screw by the motor;
an inner cannula, wherein the motor is offset from a longitudinal axis of the inner cannula; and
a penetration member; and
a coax assembly, comprising:
an outer coax cannula.

* * * * *